United States Patent
Miyake et al.

(10) Patent No.: US 6,326,168 B1
(45) Date of Patent: Dec. 4, 2001

(54) BRAIN SPECIFIC POTASSIUM CHANNEL PROTEIN

(75) Inventors: Akira Miyake; Shinobu Mochizuki; Hiromichi Yokoi, all of Ibaraki (JP)

(73) Assignee: Yamanouchi Pahrmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/600,776

(22) PCT Filed: Jan. 20, 1999

(86) PCT No.: PCT/JP99/00190

§ 371 Date: Jul. 21, 2000

§ 102(e) Date: Jul. 21, 2000

(87) PCT Pub. No.: WO99/37677

PCT Pub. Date: Jul. 29, 1999

(30) Foreign Application Priority Data

Jan. 23, 1998 (JP) .................................................. 10-011434
Dec. 4, 1998 (JP) .................................................. 10-346198

(51) Int. Cl.[7] ............................. C12P 21/06; C12P 21/04; C12N 15/00; C07H 21/04

(52) U.S. Cl. .................... 435/69.1; 435/70.3; 435/320.1; 536/23.5

(58) Field of Search ................................. 435/70.3, 69.1, 435/320.1; 536/23.5

(56) References Cited

PUBLICATIONS

Miyake, A. et al. New Ether–a–go–go K Channel Family Members Localized in Human Telecephalon (1999), J. Biol. Chem (274), pp. 25018–25025.*
Warmke et al., Afamily of potassium channel genes related to eag in Drosophila and mammals., 1994, PNAS vol. 91, 3438–3442.*
Sambrook et al., Molecular Cloning– A Laboratory Manual, 2nd Edition, 1989, 16.20, 16.30–16.40.*
International Search Report.
Antonio Castellano, et al., "Identification and Functional Characterization of a K+ Channel α–Subunit with Regulatory Properties Specific to Brain", The Journal of Neuroscience, (1997), vol. 17, No. 12, p. 4652–4661.
Jost Ludwig, et al., "Functional expression of a rat homologue of the voltage gated ether á go–go potassium channel reveals differences in selectivity and activation kinetics between the Drosophila channel and its mammalian counterpart", The EMBO Journal, (1994), vol. 13, No. 19, p. 4451–4458.
Wenmei Shi, et al., "Cloning of a mammalian elk potassium channel gene and EAG mRNA distribution in rat sympathetic ganglia", Journal of Physiology (1998), vol. 511, No. 3, p. 675–682.

Noam Meiri, et al., "Reversible antisense inhibition of Shaker–like Kv1.1 potassium channel expression impairs associative memory in mouse and rat" (Pro. Natl. Acad. Sci. USA, vol. 94, pp. 4430–4434, Apr. 1997 Cell Biology).
Nicoletta Galeottoi, et al., "An antisense Oligonucleotide on the Mouse Shaker–like Potassium Channel Kv1.1 Gene Prevents Antinociception Induced by Morphine and Baclofen"(The Journal of Pharmacology and Experimental Therapeutics, vol. 281, No. 2, pp. 941–949, 1997).
Jennifer L. Masengill, et al., "Differential Expression of $K_{4-AP}$ Currents and Kv3.1 Potassium Channel Transcripts in Cortical Neurons that Develop Distinct Firing Phenotypes"(The Journal of Neuroscience, May 1, 1997, 17(9), pp. 3136–3147).
Shan Ping Yu, et al., "Mediation of Neuronal Apoptosis by Enhancement of Outward Potassium Current"(Science, vol. 278, pp. 114–117, Oct. 3, 1997).
Irwin B. Levitan and Leonard K. Kaczmarek "The Neuron"(Cell and Molecular Biology, pp. 395–423, Oxford University Press 1991).
Kenji Sakimura, et al., "Reduced hippocampal LTP and spatial learning in mice lacking NMDA receptor ε1 subunit"(Nature, vol. 373, pp. 151–155, Jan. 12, 1995).
Joe Z. Tsien, et al., "The Essential Role of Hippocampal CA1 NMDA Receptor–Dependent Synaptic Plasticity in Spatial Memory"(Cell, vol. 87, pp. 1327–1338, Dec. 27, 1996).
Bertil Hille, "Ionic channels of Excitable Membranes, Bertil Hille/Second Edition"(Sinauer Associates, pp. 115–133, 1992).

(List continued on next page.)

Primary Examiner—Jeffrey Stucker
Assistant Examiner—Jegatheesan Seharaseyon
(74) Attorney, Agent, or Firm—Sughrue, Mion, Zinn, Macpeak & Seas, PLLC

(57) ABSTRACT

The present invention relates to a novel potassium channel protein expressed exclusively in the brain, a DNA molecule having a sequence encoding this protein, a vector containing the DNA molecule, a host cell containing this vector, and a method for obtaining the potassium channel protein, wherein mRNA is extracted from human cells or tissue capable of producing the potassium channel protein of the present invention. Then, use is made of two primers between which the channel protein mRNA or a part of the mRNA region is located by using the thus extracted mRNA as a template. By carrying out a reverse transcriptase-polymerase chain reaction, the channel protein cDNA or a part thereof can be obtained. Thereafter, the channel protein can be produced by integrating the thus obtained novel potassium channel cDNA or a part of the same into an appropriate expression vector and then effecting its expression in a host cell. The proteins are useful (1) as targets for identifying therapeutic agents for central nervous system disorders such as dementia, cerebral ischemic disorder, epilepsy and the like; (2) for use in a method of screening compounds and peptides capable of acting on the claimed protein; and (3) as agents for the treatment of central nervous system disorders.

10 Claims, 6 Drawing Sheets

PUBLICATIONS

Simon P. Aiken, et al., "Reduction of spike frequency adaptation and blockade of M–current in rat CA1 pyramidal neurones by linopirdine (DuP 996), a neurotransmitter release enhancer"(British Journal of Pharmacology, pp. 1163–1168, 1995).

Leonard Cook, et al., "Cognition Enhancement by the Acetylcholine Releaser DuP 996"(Drug Development Research, vol. 19, pp. 301–314, 1990).

Jorge D. Brioni, et al., "Linopirdine (DuP996) FacilitatEs the Retention of Avoidance Training and Improves Performance of Septal–Lesioned Rats in the Water Maze"(Pharmacology Biochemistry and Behavior, vol. 44, pp. 37–43. 1993).

Hong–Sheng Wang, et al., "KCNQ2 and KCNQ3 Potassium Channel Subunits: mOlecular Correlates of the M–Channel-"(Science, vol. 282, pp. Pp. 1890–1893, Dec. 4, 1998).

Edward C. Cooper, et al., "Colocalization and coassembly of two human brain M–type potassium channel subunits that are mutated in epilepsy"(PNAS vol. 97 No. 9, pp.4914–4919, Apr. 25, 2000).

* cited by examiner

BRAIN SPECIFIC POTASSIUM CHANNEL PROTEIN

TECHNICAL FIELD

The present invention belongs to the field of genetic engineering, and particularly relates to a novel potassium channel protein expressed exclusively in the brain, or an equivalent thereof, a gene encoding the protein or an equivalent thereof, a vector containing the gene, a host cell containing the vector, and so on.

BACKGROUND ART

Potassium channel is a protein which is distributed in the surface membrane of cells and selectively allows potassium ions to pass through it, and it is considered that it takes an important role in controlling membrane potential of cells. Particularly, in nerve and muscle cells, it contributes to the neurotransmission of central and peripheral nerves, pace making of the heart, contraction of muscles and the like by controlling frequency, persistency and the like of action potential. In addition, it has been shown that it is also concerned in the secretion of hormones, adjustment of cell volume, proliferation of cells and the like.

As the classification based on the opening and closing mechanism of the channel, a voltage-dependent potassium channel, an inwardly rectifying potassium channel, a calcium-dependent potassium channel, a receptor coupling type potassium channel and the like have so far been identified. In addition, an ATP-dependent potassium channel, a pH-dependent potassium channel and the like have also been reported. Among them, the voltage-dependent potassium channel has a characteristic in that it opens when the membrane potential is depolarized. In general, potassium ions are present in a non-equilibrium state of about 5 mM outside the cell and about 150 mM inside the cell. Thus, when the voltage-dependent potassium channel is opened by depolarization, potassium ions flow out from intracellular part to extracellular part and, as a result, induce restoration of the membrane potential (re-polarization). Accordingly, the opening of voltage-dependent potassium channel induces reduction of excitability of nerve and muscle cells and the like. Also, it causes changes in cellular functions in non-excitatory cells too, such as increase in the driving force for $Ca^{2+}$ and subsequent increase in the flow of the same ion into the intracellular part. A compound capable of modifying opening of the voltage-dependent channel has a possibility of controlling various functions of cells, including excitability of nerve and muscle cells.

Genes of some types of the voltage-dependent potassium channel have been isolated from the brain and heart, and primary structure of the protein has been revealed. Based on the primary structure, it has been suggested that the voltage-dependent potassium channel has six transmembrane domains (S1 to S6) and one ion permeation region (H5). Also, it is assumed that the fourth transmembrane domain S4 contains basic amino acids having positive charge at intervals of 3 to 4 bases and functions as a voltage sensor.

These channels are roughly divided into Shaker type and eag type, based on the similarity of amino acid sequences. The Shaker type is a family having markedly high diversity and can be further divided into four groups of Kv1, Kv2, Kv3 and Kv4. On the other hand, the eag type is constituted by eag, eag-related gene and elk, and it related genes include hyperpolarization activation type potassium channels corresponding to KAT gene cluster and a cation channel which is activated by a cyclic nucleotide.

Regarding the importance of voltage-dependent potassium current in the brain, several findings have been obtained using these cloned voltage-dependent potassium channels. For example, relationship of Kv1.1 with memory and pain has been suggested by antisense-aided in vivo experiments (Meiri, N. et al. (1997) *Proc. Natl. Acad. Sci. USA*, 94, 4430–4434; Galeotti, N. et al. (1997) *J. Pharmaco. Exp. Ther.*, 281, 941–949). Regarding Kv3.1, its participation in the excitability of GABA activating interneuron in cerebral cortex has been shown (Massengill, J. et al. (1997) *J. Neurosci.*, 3136–3147). On the other hand, some experiments carried out using tetraethylammonium and 4-aminopyridine as non-selective inhibitors of the voltage-dependent potassium channel have also been reported. It has been shown that tetraethylammonium suppresses voltage-dependent potassium current in cerebral cortex nerve cells and also inhibits apoptosis of the same nerve cells (Yu, S. P. et al. (1997), *Science*, 278, 114–117). Also, it is known that intraventricular administration of 4-aminopyridine causes epileptic attack. These results suggest a possibility that an agent capable of controlling the activity of voltage-dependent potassium channel in the brain will become a therapeutic agent for central nervous system disorders such as dementia due to disturbance of memory and so on, nerve cell death accompanied by cerebral ischemia, epilepsy and the like.

On the other hand, most of the voltage-dependent potassium channels so far cloned are distributed in a large number of tissues among organs in the whole body. Thus, even when an agent which acts selectively on a specified voltage-dependent potassium channel is found, there is a possibility that the agent acts on many tissues and thereby induces originally unexpected agent effects. In order to find an agent having less side effects by targeting a potassium channel, it is necessary to clone a potassium channel in which its expressing tissue is restricted.

DISCLOSURE OF THE INVENTION

An object of the present invention is to provide a novel potassium channel protein expressed exclusively in the brain, as a target of therapeutic agents for central nervous system disorders such as dementia, cerebral ischemic disorder, epilepsy and the like, and another object of the present invention is to provide a method for screening compounds and peptides capable of modifying activity of the same potassium channel protein, which are useful as therapeutic agents for central nervous system disorders, and a novel agent for use in the treatment of central nervous system disorders, which specifically acts upon the central nervous system and generates less side effects.

With the aim of solving the aforementioned problems, the present inventors have conducted intensive studies and, as a result, succeeded in isolating a gene coding for a novel potassium channel protein expressed exclusively in the brain. The inventors have also succeeded in expressing the novel potassium channel protein expressed exclusively in the brain and establishing a method for the screening of compounds and peptides capable of modifying activity of the same potassium channel protein.

The present invention relates to:
1) a potassium channel protein or an equivalent thereof, which has an amino acid sequence selected from either of Sequence Nos. 2 and 6, or an amino acid sequence resulting from said amino acid sequence by substitution, deletion or insertion of certain amino acid(s), and is expressed exclusively in the brain, 2) the potassium channel protein or an equivalent thereof according to the item 1), which is expressed exclusively in the human brain,
3) a potassium channel protein which has an amino acid sequence selected from either of Sequence Nos. 2 and 6, 4) a gene which has a gene sequence encoding the potassium channel protein or an equivalent thereof described in the items 1) to 3),
5) a gene which has a gene sequence encoding an amino acid sequence selected from either of Sequence Nos. 2 and 6, 6) a gene which has a gene sequence selected from either of the 6th to 3257th gene sequence of Sequence No. 1 or the 4th to 3057th gene sequence of Sequence No. 5, or a gene which is degenerate with respect to said gene,
7) a vector which contains the gene of the items 4) to 6),
8) a host cell which contains the vector of the item 7), or
9) a method for producing the potassium channel protein described in the items 1) to 3), which uses the host cell of the item 8).

The terms to be used in the present invention are explained in the following. The term "substitution, deletion or insertion of amino acid" means that one or a plurality of amino acids are substituted, deleted or inserted in the amino acid sequence selected from either of the Sequence Nos. 2 and 6.

The term "expressed exclusively in the brain" means that it is expressed in the brain but not expressed in the heart, placenta, lung, liver, skeletal muscle, kidney, pancreas, spleen, thymus, prostate, testis, ovary, small intestines, large intestine and peripheral blood leukocytes, illustratively, it means that when Northern blotting is carried out under the conditions of Examples, the signal is detected only in the brain and not detected in the heart, placenta, lung, liver, skeletal muscle, kidney, pancreas, spleen, thymus, prostate, testis, ovary, small intestines, large intestine and peripheral blood leukocytes.

Also, the term "equivalent" means a protein having a sequence in which one or a plurality of amino acids are substituted, deleted or inserted in the amino acid sequence of the protein which is expressed in the brain but not expressed in the heart, placenta, lung, liver, skeletal muscle, kidney, pancreas, spleen, thymus, prostate, testis, ovary, small intestines, large intestine and peripheral blood leukocytes, but still having the same functions when compared with the protein without alteration of its amino acid sequence.

The term "human origin" means that it is the same amino acid sequence of a potassium channel protein expressed in human.

In this connection, the potassium channel and the potassium channel protein are used as synonyms.

The novel potassium channel protein of the present invention or an equivalent thereof may be any potassium channel protein or an equivalent thereof, with the proviso that it is expressed exclusively in the brain, but is preferably a human origin. Illustratively, a potassium channel protein or an equivalent thereof, which has an amino acid sequence selected from either of Sequence Nos. 2 and 6, or has an amino acid sequence in which one or a plurality of amino acids in the amino acid sequence selected from either of Sequence Nos. 2 and 6 are substituted, deleted or inserted, and is expressed exclusively in the brain, is included in the present invention and is preferably a human origin. More preferred is a potassium channel protein which has an amino acid sequence selected from either of Sequence Nos. 2 and 6.

The gene which has a gene sequence encoding the novel potassium channel protein of the present invention or an equivalent thereof may be any gene which has a gene sequence encoding a potassium channel protein or an equivalent thereof expressed exclusively in the brain, but is preferably a gene which encodes a potassium channel protein of human origin. Illustratively, a gene which encodes a potassium channel protein or an equivalent thereof having an amino acid sequence selected from either of Sequence Nos. 2 and 6, or a gene which encodes a potassium channel protein or an equivalent thereof having an amino acid sequence in which one or a plurality of amino acids in the amino acid sequence selected from either of Sequence Nos. 2 and 6 are substituted, deleted or inserted, and is expressed exclusively in the brain, is included in the present invention, and the gene is preferably a gene which encodes a human origin potassium channel protein or an equivalent thereof. More preferred is a gene which encodes an amino acid sequence selected from either of Sequence Nos. 2 and 6. Most preferred is a gene which has a gene sequence selected from either of the 6th to 3257th gene sequence of Sequence No. 1 or the 4th to 3057th gene sequence of Sequence No. 5. Also included in the present invention is a gene which hybridizes with the gene of Sequence No. 1 or 5 under a stringent condition.

Hybridization can be carried out in accordance with a known method (Maniatis, T. et al. (1982): "Molecular Cloning—A Laboratory Manual", Cold Spring Harbor Laboratory, NY). The term "stringent condition" means a condition that a sample after hybridization is washed twice in 2×SSC containing 0.1% SDS and then subjected to the following washing step.

This washing step means that the washing (65° C.) is carried out in 0.5×SSC containing 0.1% SDS, preferably in 0.2×SSC containing 0.1% SDS, most preferably in 0.1×SSC containing 0.1% SDS. A gene which encodes the novel potassium channel protein of the present invention can be obtained by the following methods.

1) Method for Producing Novel Potassium Channel Gene
a) First Production Method mRNA is extracted from human cells or tissue capable of producing a novel potassium channel protein. Two primers between which the channel protein MRNA or a part of the mRNA region is located are used with the thus extracted mRNA as a template. By carrying out a reverse transcriptase-polymerase chain reaction (to be referred to as RT-PCR hereinafter), the channel protein cDNA or a part thereof can be obtained. Thereafter, the channel protein can be produced by integrating the thus obtained novel potassium channel cDNA or a part of the same into an appropriate expression vector to carry out its expression in a host cell.

Firstly, from human cells or tissue capable of producing the novel potassium channel protein of the present invention, such as human cerebral cortex, mRNA containing that encoding the protein is extracted by a known method. Guanidine thiocyanate-hot phenol method, guanidine thiocyanate-guanidine hydrochloride method and the like can be exemplified as the extraction method, but guanidine thiocyanate-cesium chloride method can be cited as a preferred method. The cells or tissue capable of producing the protein can be identified, for example, by a western blotting method which uses an antibody specific for the protein.

Purification of the MRNA can be made in accordance with a usual method, for example, the mRNA can be purified by the adsorption and elution using an oligo(dT)-cellulose column. The mRNA can be further fractionated by a sucrose density gradient centrifugation or the like.

Alternatively, a commercially available mRNA extracted sample may be used without carrying out the extraction of the mRNA.

Next, single-stranded cDNA is synthesized by carrying out reverse transcriptase reaction of the thus purified mRNA in the presence of a random primer or an oligo dT primer. This synthesis can be carried out in the usual way. The thus obtained single-stranded cDNA is subjected to PCR using two primers between which a partial region of the gene of interest is located, thereby amplifying the novel potassium channel DNA of interest. The thus obtained DNA is fractionated by an agarose gel electrophoresis or the like. As occasion demands, a DNA fragment of interest can be obtained by carrying out digestion of the DNA with restriction enzymes and subsequent ligation.

b) Second Production Method

In addition to the above production method, the gene of the present invention can also be produced using conventional genetic engineering techniques. Firstly, single-stranded cDNA is synthesized using reverse transcriptase, making use of the mRNA obtained by the aforementioned method as a template, and then double-stranded cDNA is synthesized from the single-stranded cDNA. Examples of this method include SI nuclease method (Efstratiadis, A. et al. (1976), *Cell*, 7, 279–288), Land method (Land, H. et al. (1981), *Nucleic Acids Res.*, 9, 2251–2266), O. Joon Yoo method (Yoo, O. J. et al. (1983), *Proc. Natl. Acad. Sci. USA*, 79, 1049–1053) and Okayama-Berg method (Okayama, H. and Berg, P. (1982), *Mol. Cell. Biol.*, 2, 161–170).

Next, the recombinant plasmid obtained by the above method is introduced into an Escherichia coli strain, such as DH 5α, to effect its transformation, and then a transformant can be selected making use of tetracycline resistance or ampicillin resistance as a marker. When the host cell is *E. coli*, transformation of the host cell can be carried out, for example, by the method of Hanahan (Hanahan, D. (1983), *J. Mol. Biol.*, 166, 557–580), namely a method in which the recombinant DNA is added to competent cells prepared in the presence of $CaCl_2$ and $MgCl_2$ or $RbCl$. In this connection, phage vectors such as a lambda system or the like can also be used as the vector in addition to a plasmid.

Regarding the method for selecting a strain containing DNA which encodes the novel potassium channel protein of interest from the transformants obtained above, various methods such as those shown below can be employed.

(i) A Screening Method which uses a synthetic Oligonucleotide Probe

An oligonucleotide which corresponds to the entire portion or a part of the novel potassium channel protein is synthesized (in this case, it may be either a nucleotide sequence taking the codon usage into consideration or a plurality of nucleotide sequences as a combination of possible nucleotide sequences, and in the latter case, their numbers can be reduced by including inosine) and, using this as a probe (labeled with $^{32}P$ or $^{33}P$), hybridized with transformant DNA samples denatured and fixed on a nitrocellulose filter and the resulting positive strains are screened and selected.

(ii) A Screening Method which uses a Probe Prepared by Polymerase Chain Reaction Oligonucleotides of sense primer and antisense primer corresponding to a part of the novel potassium channel protein are synthesized, and a DNA fragment which encodes the entire portion or a part of the novel potassium channel protein of interest is amplified by carrying out polymerase chain reaction (Saiki, R. K. et al. (1988), *Science*, 239, 487–491) using these primers in combination. As the template DNA to be used herein, cDNA synthesized by reverse transcription reaction from mRNA of cells capable of producing the novel potassium channel protein, or genomic DNA, can be used. The thus prepared DNA fragment is labeled with $^{32}P$ or $^{33}P$, and the clone of interest is selected by carrying out colony hybridization or plaque hybridization using this fragment as a probe.

(iii) A Method in which Screening is Carried out by Producing the Novel Potassium Channel Protein in Other Animal Cells Genes are amplified by culturing the transformants, and transfection of animal cells with the genes is carried out (in this case, either a plasmid which can replicate by itself and contains a transcription promoter region or a plasmid which can be integrated into the chromosome of animal cells may be used), thereby effecting production of proteins encoded by the genes on the cell surface. A strain containing cDNA which encodes the novel potassium channel protein of interest is selected by detecting the protein using an antibody for the novel potassium channel protein, or from the original transformants using the channel activity as a marker.

(iv) A Method in which the Selection is Carried out Using Channel Activity for the Novel Potassium Channel Protein as a Marker cDNA is integrated into an expression vector in advance, proteins are produced on the cell surface of transformants, and the strain of interest is selected by detecting desired novel potassium channel protein producing strains using the channel activity as a marker.

(v) A Method in which the Selection is Carried out Using an Antibody for the Novel Potassium Channel Protein cDNA is integrated into an expression vector in advance, proteins are produced on the cell surface of transformants, and the strain of interest is selected by detecting desired novel potassium channel protein producing strains using an antibody for the novel potassium channel protein and a second antibody for the first antibody.

(vi) A Method which uses a Selective Hybridization Translation System cDNA obtained from each transformant is blotted for example on a nitrocellulose filter and hybridized with mRNA prepared from the novel potassium channel protein producing cells, and then the mRNA bonded to the cDNA is dissociated and recovered. The thus recovered MRNA is translated into protein in a protein translation system such as injection into Xenopus oocyte or a cell-free system such as a rabbit reticulocyte lysate, wheat germ or the like. A strain of interest is selected by the detection using an antibody for the novel potassium channel protein.

The method for collecting DNA which encodes the novel potassium channel protein from the thus obtained transformant of interest can be carried out in accordance with a known method (Maniatis, T. et al. (1982): "Molecular Cloning—A Laboratory Manual", Cold Spring Harbor Laboratory, NY). For example, it can be made by separating a fraction corresponding to the plasmid DNA from cells and cutting out the cDNA region from the plasmid DNA.

The method for collecting DNA which encodes the novel potassium channel protein from the thus obtained transformant of interest can be carried out in accordance with a known method (Maniatis, T. et al. (1982): "Molecular Cloning—A Laboratory Manual", Cold Spring Harbor Laboratory, NY). For example, it can be made by separating a fraction corresponding to the plasmid DNA from cells and cutting out the cDNA region from the plasmid DNA.

c) Third Production Method

The DNA having a nucleotide sequence which encodes the amino acid sequence selected from either of Sequence Nos. 2 and 6 can also be produced by binding a gene fragment produced by a chemical synthesis method. Each DNA can be synthesized using a DNA synthesizer (e.g., Oligo 1000M DNA Synthesizer (Beckman) or 394 DNA/RNA Synthesizer (Applied Biosystems)).

d) Fourth Production Method

In order to effect expression of the novel potassium channel protein function expressed exclusively in the brain by the substance obtained by genetic engineering techniques making use of the DNA of the present invention, it is not always necessary to have entire portion of the amino acid sequence selected from either of Sequence Nos. 2 and 6; for example, when a part of the sequence shows functions of the novel potassium channel protein expressed exclusively in the brain, such an amino acid sequence is also included in the potassium channel protein of the present invention. Also, as is known in the interferon gene and the like, it is considered that genes of eucaryote generally show polymorphism (e.g., see Nishi, T. et al. (1985), *J. Biochem.*, 97, 153–159), so that there will be a case in which one or a plurality of amino acids are substituted due to the polymorphism or a case in which the nucleotide sequence is changed but the amino acids are not changed. In consequence, even in the case of a protein in which one or a plurality of amino acid residues are substituted, deleted or inserted at one or a plural positions in the amino acid sequence selected from either of Sequence Nos. 2 and 6, it is possible that it has the channel activity and is expressed exclusively in the brain. In the present invention, such a protein is called an equivalent of the novel potassium channel protein.

All genes which encode such equivalents of the novel potassium channel protein and have equivalent nucleotide sequences are included in the present invention. These various types of DNA of the present invention can also be produced by nucleic acid chemical synthesis in accordance with a usual method such as phosphite triester method (Hunkapiller, M. et al. (1984), *Nature*, 10, 105–111), based on the information on the aforementioned novel potassium channel protein. In this connection, codons for each amino acid are well known and can be optionally selected and determined in the usual way, for example by taking codon usage of each host to be used into consideration (Crantham, R. et al. (1981), *Nucleic Acids Res.*, 9, r43–r74). In addition, partial modification of codons of these nucleotide sequences can be carried out in accordance with a usual method such as site specific mutagenesis which uses a primer comprised of a synthetic oligonucleotide coding for a desired modification (Mark, D. F. et al. (1984), *Proc. Natl. Acad. Sci. USA*, 81, 5662–5666).

Determination of the DNA sequences obtained by the above methods a) to d) can be carried out by, for example, the Maxam-Gilbert chemical modification method (Maxam, A. M. and Gilbert, W. (1980): "Methods in Enzymology" 65, 499–559) or the dideoxynucleotide chain termination method which uses M13 (Messing, J. and Vieira, J (1982), *Gene*, 19, 269–276).

Also, the vector of the present invention, the host cell of the present invention and the potassium channel protein of the present invention can be obtained by the following methods.

2) Method for Producing Recombinant Protein of the Novel Potassium Channel

An isolated fragment containing a gene coding for the novel potassium channel protein can transform a host cell of other eucaryote by re-integrating it into an appropriate vector DNA. Also, it is possible to effect expression of the gene in respective host cell, by introducing an appropriate promoter and a sequence related to the gene expression into the vector.

Cells of vertebrates, insects, yeast and the like are included in the eucaryotic host cells, and COS cell as a simian cell (Gluzman, Y. (1981), *Cell*, 23, 175–182), a dihydrofolate reductase defective strain of Chinese hamster ovary cell (CHO) (Urlaub, G. and Chasin, L.A. (1980), *Proc. Natl. Acad. Sci. USA*, 77, 4216–4220) and the like are frequently used as the vertebral cells, though not limited thereto.

The expression vector which can be used in vertebral cells generally has a promoter positioned at the upstream of the gene to be expressed, an RNA splicing region, a polyadenylation region, a transcription termination sequence and the like, and it may further have a replication origin as occasion demands. Examples of the expression vector include pSV2dhfr which has SV40 early promoter (Subramani, S. et al. (1981), *Mol. Cell. Biol.*, 1, 854–864), though not limited thereto.

When COS cell is used as the host cell, a vector which has the SV40 replication origin, can perform autonomous replication and has a transcription promoter, a transcription termination signal and an RNA splicing region can be used as the expression vector, and its examples include pME18S (Maruyama, K. and Takebe, Y. (1990), *Med. Immunol.*, 20, 27–32), pEF-BOS (Mizushima, S. and Nagata, S. (1990), *Nucleic Acids Res.*, 18, 5322), pCDM8 (Seed, B. (1987), *Nature*, 329, 840–842) and the like. The expression vector can be incorporated into COS cell, for example, by DEAE-dextran method (Luthman, H. and Magnusson, G. (1983), *Nucleic Acids Res.*, 11, 1295–1308), calcium phosphate-DNA co-precipitation method (Graham, F. L. and van der Ed, A. J. (1973), *Virology*, 52, 456–457) or electroporation (Neumann, E. et al. (1982), *EMBO J.*, 1, 841–845), thereby obtaining a desired transformant cell. Also, when CHO cell is used as the host cell, a transformant cell capable of stably producing the novel potassium channel protein can be obtained by carrying out co-transfection of a expression vector together with a vector capable of expressing neo gene which functions as a G418 resistance marker, such as pRSVneo (Sambrook, J. et al. (1989): "Molecular Cloning—A Laboratory Manual", Cold Spring Harbor Laboratory, NY) or pSV2-neo (Southern, P. J. and Berg, P. (1982), *J. Mol. Appl. Genet.*, 1, 327–341) or the like, and selecting G418 resistant colonies.

The thus obtained transformant of interest can be cultured in the usual way, and the novel potassium channel protein is produced inside the cells or on the cell surface. Regarding the medium to be used in the culturing, it can be optionally selected from various commonly used types depending on the host cell used, and in the case of the aforementioned COS cell for example, a medium such as RPMI-1640 medium, Dulbecco's modified Eagle's minimum essential medium (DMEM) or the like can be used by supplementing it with serum component such as fetal bovine serum (FBS) or the like as occasion demands.

The novel potassium channel protein thus produced in the cells or on the cell surface of the transformant can be separated and purified therefrom by various known separation techniques making use of the physical properties, chemical properties and the like of the channel protein. Illustrative examples of such techniques, to be carried out after solubilization of the channel protein-containing membrane fraction, include usual treatment with a protein precipitant, ultrafiltration, various liquid chromatography techniques such as molecular sieve chromatography (gel filtration), adsorption chromatography, ion exchange chromatography, affinity chromatography, high performance liquid chromatography (HPLC) and the like, dialysis and combinations thereof. In this connection, the membrane fraction can be obtained in the usual way. For example, it can be obtained by culturing the cells which expressed the novel potassium channel protein on the cell surface, suspending them in a buffer and then homogenizing and centrifuging them. Also, when the channel protein is solubilized using a solubilizing agent as mild as possible (CHAPS, Triton X-100, digitonin or the like), characteristics of the channel can be maintained after the solubilization.

A method for the screening of compounds and peptides capable of modifying activities of the potassium channel protein is included in the present invention. This screening method includes a means of adding an agent to be tested to the system and measuring the index, in which an index of the modification of potassium channel protein in response to a physiological characteristic of the potassium channel protein is measured making use of the thus constructed potassium channel protein which is expressed exclusively in the brain. The following screening methods can be cited as illustrative examples of this measuring system. Also, examples of the agents to be tested include compounds or peptides which are conventionally known to have potassium channel ligand activities but their ability to selectively modify activities of the potassium channel protein expressed exclusively in the brain is not clear (e.g., compounds described in JP-A-4-178375; the term "JP-A" as used herein means an "unexamined published Japanese patent application"), various known compounds and peptides registered in chemical files but their potassium channel ligand activities are unknown, compounds obtained by combinatorial chemistry techniques and random peptides prepared by employing a method such as phage display and the like. In addition, culture supernatants of microorganisms and natural components originated from plants and marine organisms are also objects of the screening. Also useful are compounds or peptides obtained by chemically or biologically modifying a compound or peptide selected by the screening method of the present invention.

3) Method for the Screening of Compounds and Peptides Capable of Modifying Activities of the Novel Potassium Channel Protein a) Screening Method to which Voltage-Clamp Method is Applied Channel activities of the novel potassium channel protein can be measured by the whole-cell voltage-clamp method. Cells in which the channel protein is expressed are subjected to membrane potential fixation by the whole-cell voltage-clamp method and whole-cell current is measured. A solution containing 145 mM NaCl, 5.4 mM KCl, 2 mM $CaCl_2$ and 0.8 mM $MgCl_2$ is used as the extracellular liquid, and a solution containing 155 mM KCl is used as the intracellular liquid (patch electrode solution). Compounds and peptides capable of modifying activities of the novel potassium channel protein can be screened by comparing outward currents generated by a depolarization stimulus, namely shifting of membrane potential from the holding potential (e.g., –70 mV) to the depolarization side (e.g., –80 mV), in the presence and absence of an agent to be tested.

b) Screening Method utilizing $Rb^+$ ion Release

In general, the potassium channel can pass $Rb^+$ ion similar to $K^+$ ion, so that its channel activity can be measured using radioactive isotope $^{86}Rb^+$ release as an index. By carrying out incubation of novel potassium channel protein-expressed cells together with $^{86}RbCl$ (e.g., 18 hr at 37° C.), $^{86}Rb^+$ can be incorporated into the cells. The cells are washed with low $K^+$ concentration physiological saline (e.g., 4.5 mM $K^+$) and then suspended in the same solution. When a high $K^+$ concentration solution (e.g., 100 mM in final concentration) is added to the cell suspension, membrane potential of the cells is depolarized and the potassium channel is activated. Since $^{86}Rb^+$ inside the cells is thereby released into the extracellular moiety, the radioactivity in the extracellular liquid can be used as an index of the channel activity. Compounds and peptides capable of modifying activity of the novel potassium channel protein can be screened by comparing radioactivity released into the extracellular moiety when the high $K^+$ concentration solution is added, in the presence and absence of an agent to be tested.

c) Screening Method which uses Voltage-Sensitive Ddye or Intracellular $K^+$ Detecting Dye A voltage-sensitive dye or a intracellular $K^+$ detecting dye can optically detect changes in the membrane potential or intracellular $K^+$ concentration accompanied by the opening of the potassium channel. As the voltage-sensitive dye, RH155, WW781, Di-4-ANEPPS or derivatives thereof can be used. Also, a chimeric protein prepared by inserting the amino acid sequence of green fluorescent protein into the C-terminal intracellular region of Shaker type voltage-dependent potassium channel can be used for the detection of membrane potential (Siegel, M. S. and Isacoff, E. Y. (1997), *Neuron*, 19, 735–741). As the intracellular $K^+$ detecting dye, $K^+$-binding benzofuran isophthalate and the like can be used. Since channel activity of the novel potassium channel can be measured by the use of these dyes, compounds and peptides capable of modifying activity of the novel potassium channel protein can be screened by comparing the changing amounts in the presence and absence of an agent to be tested.

A medicament which contains a compound or peptide capable of significantly modifying the activity of potassium channel protein exclusively expressed in the brain, selected by the aforementioned screening as an active ingredient, is included in the present invention.

The medicament of the present invention is characterized in that it has novel pharmacological action to selectively control activities of potassium channel in the brain, and the use of the medicament is for diseases caused by abnormalities (e.g., acceleration, reduction, and denaturation) of potassium channel activities in the brain or those which express and complicate such abnormalities, wherein their illustrative examples include central nervous system disorders such as dementia, cerebral ischemic disorder, epilepsy and the like.

The pharmaceutical preparation which contains a compound or peptide capable of modifying activity of the potassium channel protein of the present invention, as an active ingredient, can be prepared using carriers, fillers and other additives generally used in the preparation of medicaments, in response to each type of the active ingredient.

Examples of its administration include oral administration by tablets, pills, capsules, granules, fine granules, powders, oral solutions and the like, and parenteral administration by injections (e.g., intravenous, intramuscular or the like), suppositories, transdermal preparations, transmucosal absorption preparations and the like. Particularly, in the case of peptides which are digested by gastric acid, parenteral administration such as intravenous injection or the like, or lower gastrointestinal delivery administration is desirable.

In the solid composition for use in the oral administration according to the present invention, one or more active substances are mixed with at least one inert diluent such as lactose, mannitol, glucose, microcrystalline cellulose, hydroxypropylcellulose, starch, polyvinyl pyrrolidone or aluminum magnesium silicate. In the usual way, the composition may contain other additives than the inert diluent, such as a lubricant, a disintegrating agent, a stabilizing agent and a solubilizing or solubilization assisting agent. If necessary, tablets or pills may be coated with a sugar coating or a film of a gastric or enteric substance.

The liquid composition for oral administration includes emulsions, solutions, suspensions, syrups and elixirs and contains a generally used inert diluent such as purified water or ethyl alcohol. In addition to the inert diluent, this composition may also contain other additives such as moistening agents, suspending agents, sweeteners, flavors and antiseptics.

The injections for parenteral administration includes aseptic aqueous or non-aqueous solutions, suspensions and emulsions. Examples of the diluent for use in the aqueous solutions and suspensions include distilled water for injection use and physiological saline. Examples of the diluent for use in the non-aqueous solutions and suspensions include propylene glycol, polyethylene glycol, plant oil (e.g., olive oil or the like), alcohols (e.g., ethanol or the like), polysorbate 80 and the like. Such a composition may further contain a moistening agent, an emulsifying agent, a dispersing agent, a stabilizing agent, a solubilizing or solubilization assisting agent, an antiseptic and the like. These compositions are sterilized for example by filtration through a bacteria retaining filter, blending of a germicide or irradiation. Alternatively, they may be used by firstly making into sterile solid compositions and dissolving them in sterile water or other sterile solvent for injection use prior to their use.

The dose is optionally decided by taking into consideration strength of each active ingredient selected by the aforementioned screening method and symptoms, age, sex and the like of each patient to be administered.

BRIEF DESCRIPTION OF THE DRAWINGS

FIG. 1 shows amino acid sequences of Sequence No. 2 (upper line) and Sequence No. 6 (lower line) potassium channels.

BEST MODE FOR CARRYING OUT THE INVENTION

Figure 2:
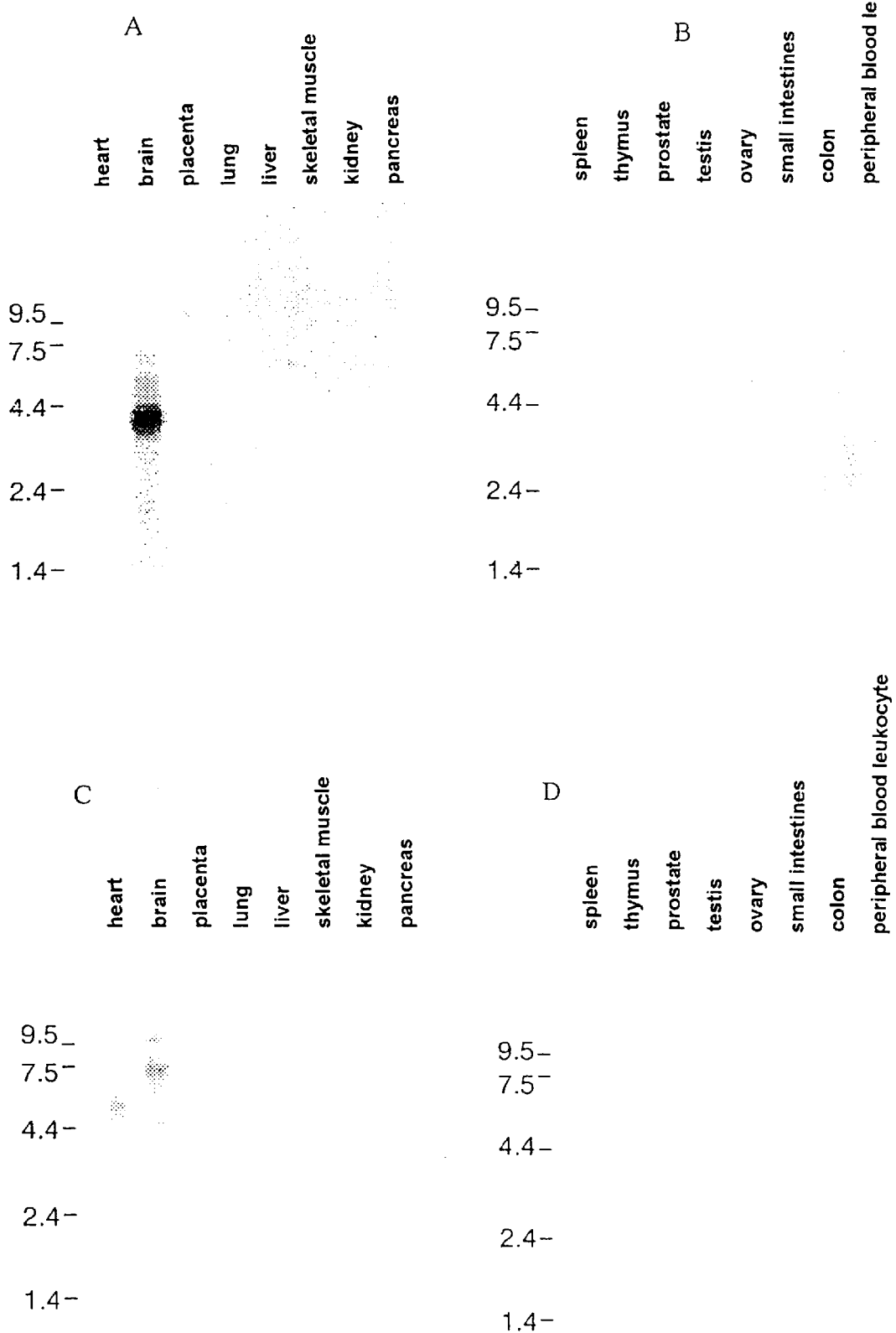
FIG. 2 shows results of Northern analysis on the novel potassium channel in each human organ. A and B represent results on the potassium channel of Sequence No. 2, and C and D on the potassium channel of Sequence No. 6.

In order to disclose the present invention more illustratively, examples are described in the following, but the present invention is not limited to the examples. In this connection, unless otherwise noted, they can be carried out in accordance with known methods (Maniatis, T. et al. (1982): "Molecular Cloning—A Laboratory Manual", Cold Spring Harbor Laboratory, NY).

EXAMPLE 1

Isolation of Gene Encoding the Novel Potassium Channel Protein

The full-length CDNA encoding the novel potassium channel protein was obtained by RT-PCR using human brain poly $A^+RNA$ (Clontech) as a template.

In order to isolate gene of the potassium channel protein shown in Sequence No. 2, 5'-GGAATTCC CTA AGA TGC CGG CCA TGC-3' (Sequence No. 3) was used as a forward primer, and 5'-GCTCTAGAGC ACT CTG AGG TTG GGC CGAAC-3' (Sequence No. 4) as a reverse primer (EcoRI site and XbaI site are added to respective 5'-termini). RT-PCR was carried out by Hot Start method using Pfu DNA polymerase (Stratagene). After carrying out first thermal denaturation at 96° C. (1 minute), a cycle of 96° C. (10 seconds)/68° C. (30 seconds)/72° C. (7 minutes) was repeated 35 times. As a result, a DNA fragment of about 3.3 kbp was amplified. This fragment was digested with EcoRI and xbaI and then cloned using pME18S plasmid. Since the pME18S plasmid contains SR promoter which shows strong promoter activity in animal cells (Takebe, Y. et al. (1988), *Mol. Cell. Biol.*, 8, 466–472), it can be used for expressing recombinant protein in animal cells. This plasmid was received from Dr. Saito at Chiba University (Maruyama, K and Takebe, Y. (1990), *Med. Immunol.*, 20, 27–32). Nucleotide sequence of the thus obtained clone pME-E1 was analyzed by dideoxy terminator method using ABI377 DNA Sequencer (Applied Biosystems). The thus revealed sequence is shown in Sequence No. 1 of Sequence Listing.

This sequence has a 3252-base open reading frame (from the 6th to 3257th of Sequence No. 1). The amino acid sequence (1083 amino acids) deduced from the open leading frame is shown in Sequence No. 2 in the Sequence Listing.

In order to isolate gene of the potassium channel protein shown in Sequence No. 6, 5'-GCC ATG CCG GTC ATG AAG G-3' (Sequence No. 7) was used as a forward primer, and 5'-GCC AGG GTC AGT GGA ATG TG-3' (Sequence No. 8) as a reverse primer. RT-PCR was carried out by Hot Start method using TaKaRa LA Taq (Takara Shuzo). After carrying out first thermal denaturation at 98° C. (1 minute), a cycle of 98° C. (15 seconds)/68° C. (3 minutes) was repeated 35 times and then finally 10 minutes of extension reaction was carried out at 72° C. As a result, a DNA fragment of about 3.1 kbp was amplified. This fragment was cloned using pCR2.1 plasmid (Invitrogen). Nucleotide sequence of the thus obtained clone is shown in Sequence No. 5 of Sequence Listing. In order to express the gene in animal cells, it was subcloned in pME18S plasmid and named pME-E2. The Sequence No. 5 contains an open reading frame of 3,054 bases (from 4th to 3057th positions of Sequence No. 5). Amino acid sequence deduced from the open reading frame (1,017 amino acids) is shown in Sequence No. 6 of Sequence Listing.

Both of the amino acid sequences of the potassium channels have six hydrophobic regions considered to be transmembrane domains (S1 to S6) which are characteristic of voltage-dependent potassium channel. Also, the S4 domain which is considered to be a voltage sensor has a characteristic in that basic amino acids are continued at an interval of 3 amino acids, and a moderately basic sequence which corresponds to the H5 region is also present between S5 and S6. In addition, both amino acid sequences have high mutual homology. Results of the alignment of both amino acid sequences are shown in FIG. 1. Their homology was 48% with the entire amino acid sequences and 70% with the hydrophobic regions (from 227 position Trp to 508 position Tyr of Sequence No. 2 and from 229 position Trp to 482 position Tyr of Sequence No. 6). In this case, MegAlign program of an analyzing software Lasergene (DNASTAR) was used in the analyses of sequence alignment and homology.

EXAMPLE 2

Distribution of Novel Potassium Channel Gene Expression in Human Tissues

Distribution of the novel potassium channel gene expression was analyzed by Northern blot hybridization. A cDNA fragment corresponding to the C-terminal intracellular region (from 2105th to 2956th positions of Sequence No. 1 for the potassium channel of Sequence No. 2, or from 2241st to 2898th positions of Sequence No. 5 for the potassium channel of Sequence No. 6) was used as a probe. Hybridization of the probe with a membrane on which poly $A^+RNA$ (2 µg) of each human organ had been blotted was carried out at 42° C. (18 hours) in a solution containing 50% formamide, 5×SSPE, 10×Denhardt's solution, 2% SDS and 100 µg/ml of denatured salmon sperm DNA. The membrane was finally washed twice with a solution containing 0.1× SSC and 0.1% SDS (at 55° C. on the potassium channel of Sequence No. 2 and at 60° C. on the potassium channel of Sequence No. 6, each for 30 minutes).

When Northern analysis was carried out on various human organs (the heart, brain, placenta, lung, liver, skeletal muscle, kidney, pancreas, spleen, thymus, prostate, testis, ovary, small intestines, large intestine and peripheral blood leukocyte), a signal of about 4 kb on the potassium channel of Sequence No. 2 and signals of about 4.4 kb and about 7.5 kb on the potassium channel of Sequence No. 6 were detected, all in the brain alone (FIG. 2). That is, it was found that the mRNA of both of the novel potassium channels is expressed exclusively in the brain. In this connection, selective expression of the Sequence No. 6 potassium channel mRNA in the brain was confirmed also by RT-PCR analysis.

Figure 3:
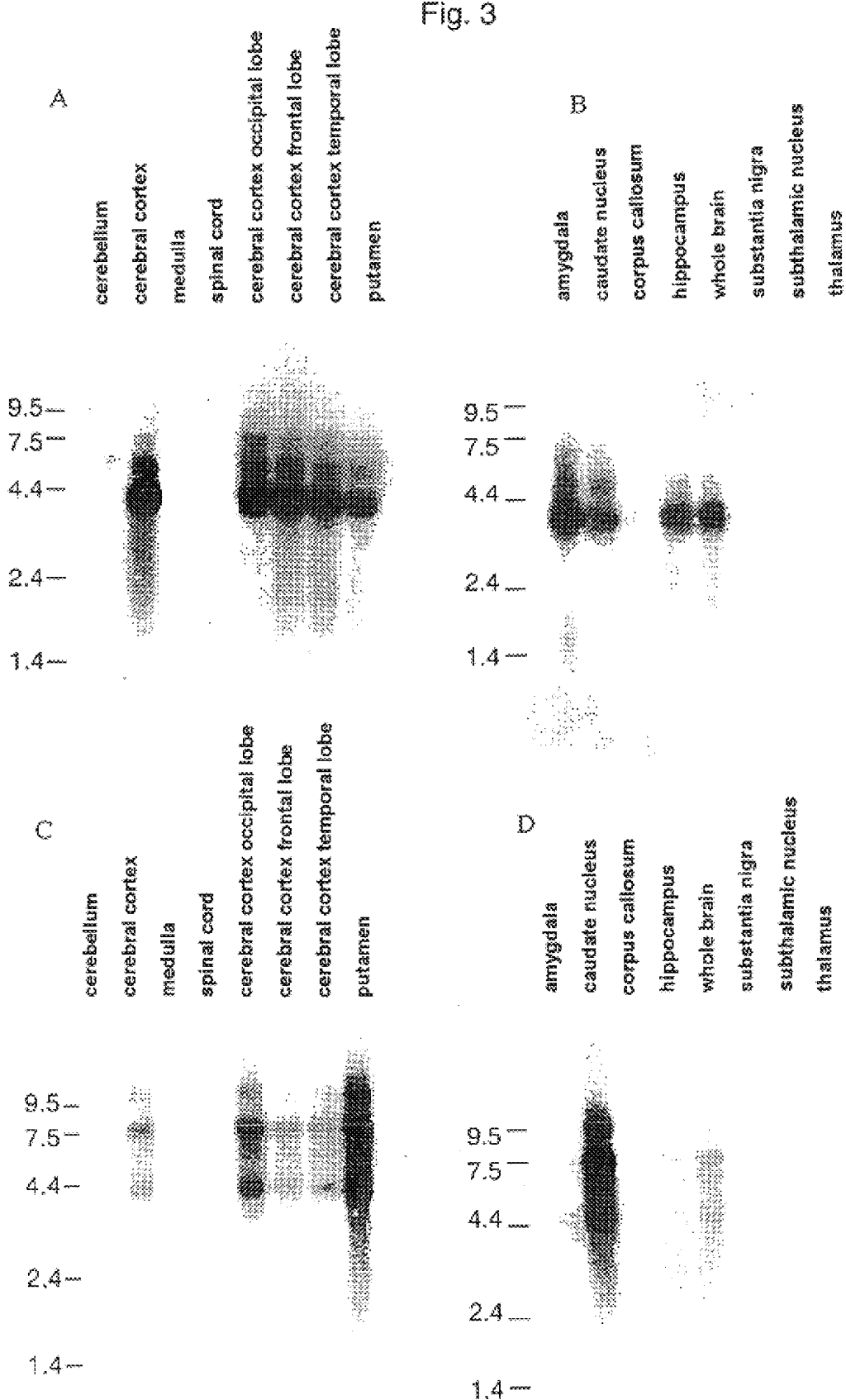
FIG. 3 shows results of Northern analysis on the novel potassium channel in each region of the human brain. A and B represent results on the potassium channel of Sequence No. 2, and C and D on the potassium channel of Sequence No. 6.

In addition, the Northern analysis was carried out also on various regions of the human brain (cerebellum, cerebral cortex, medulla, spinal cord, cerebral cortex occipital lobe, cerebral cortex frontal lobe, cerebral cortex temporal lobe, putamen, amygdala, caudate nucleus, corpus callosum, hippocampus, substantia nigra, subthalamic nucleus and thalamus). It was found that MRNA of the potassium channel shown in Sequence No. 2 is expressed exclusively in the telencephalon including cerebral cortex, caudate nucleus, hippocampus and striatum (putamen and caudate nucleus) (FIG. 3 A and B). On the other hand, it was found that mRNA of the potassium channel shown in Sequence No. 6 is expressed frequently in striped body and cerebral cortex (FIG. 3 C and D). Also, weak expression was found in hippocampus and amygdala. Distributions of both potassium channel genes were overlapped.

EXAMPLE 3

Distribution of Novel Potassium Channel Expression in Neurons of the Central Nervous System In order to examine expression of the novel potassium channel gene in neurons of the central nervous system, in situ hybridization analysis of rat brain sections was carried out. The in situ hybridization was carried out in accordance with a report (Okumura, K. et al. (1997), *Oncogene*, 14, 713–720) using an antisense RNA probe labeled with digoxigenin. A sense probe was used in the control test. These probes were prepared based on a rat potassium channel gene sequence revealed by the following procedure.

In order to obtain partial sequences of rat potassium channel genes, RT-PCR was carried out using 5'-ACC TTC CTG GAC ACC ATC GC-3' (Sequence No. 11) and 5'-CCA AAC ACC ACC GCG TGC AT-3' (Sequence No. 12) as primers. Both primers correspond to a region of from 14 to 20 positions and a region of from 493 to 499 positions of the amino acid sequence of Sequence No. 2, respectively. As a result of carrying out RT-PCR using poly $A^+RNA$ isolated from rat brain as a template, fragments of about 1.5 kb and about 1.4 kb respectively corresponding to rat orthologous genes of the potassium channels described in Sequence No. 2 and Sequence No. 6 were obtained. Next, based on the nucleotide sequences revealed from the respective fragments, RACE was carried out on them to reveal complete length sequences. RACE was carried out using Rat Brain Marathon-Ready cDNA (Clontech) in accordance with the manufacturer's instruction. Sequence of the rat orthologous gene of the potassium channel described in Sequence No. 2 is shown in Sequence No. 9, and sequence of the rat orthologous gene of the potassium channel described in Sequence No. 6 is shown in Sequence No. 10.

Figure 4:
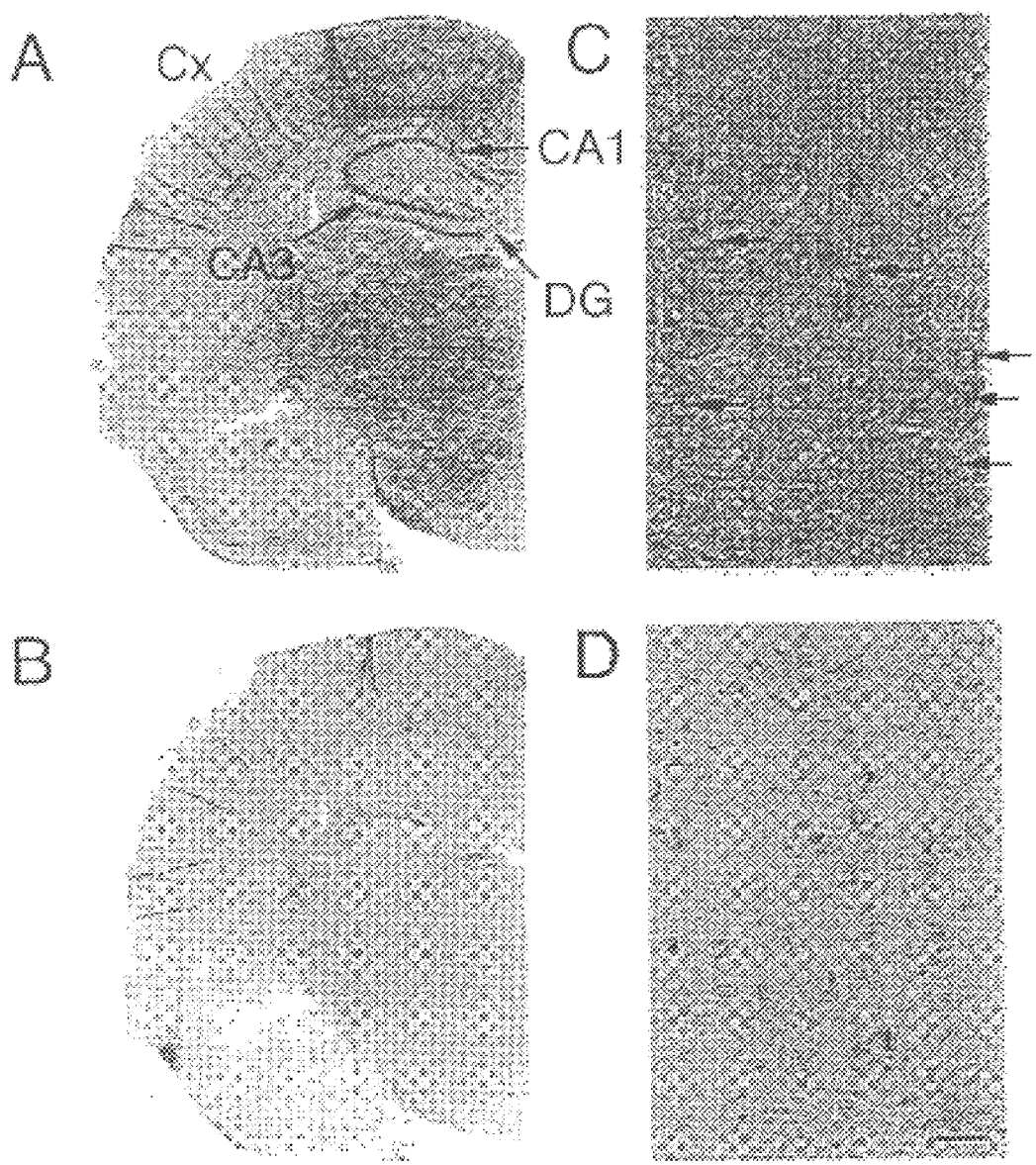
In FIG. 4, A and B show results of in situ hybridization regarding potassium channel (Sequence No. 2) (DG, the granule cell layer of the dentate gyrus; CA1 and CA3, the pyramidal cell layer of the CA1 and CA3 fields of Ammon's horn; Cx, cerebral cortex). C and D represent enlarged images of cerebral cortex (arrows indicate signals in typical pyramidal cells). An antisense probe (in A and C) or a sense probe (in B and D) was used in the hybridization. The scale bar indicates 1.5 mm (A and B) or 50 $\mu$m (B and D).

An antisense sequence or sense sequence of from 2,683 to 3,204 positions of Sequence No. 9 was used as a probe for the aforementioned rat orthologous gene of the potassium channel described in Sequence No. 2. As a result of the in situ hybridization, signals were observed in hippocampus only when the antisense probe was used, and the expression was confirmed in the same region (FIG. 4 A and B). The expression in hippocampus was observed in granule cells of the dentate gyrus, pyramidal cells of the CA1 and CA3 fields of Ammon's horn and the like neurons. Specific signals were also observed in pyramidal cells as neurons of cerebral cortex (FIG. 4 C and D). Thus, it was confirmed that the potassium channel is expressed in the neurons of the central nervous system.

A sequence of from 3,140 to 3,750 positions of Sequence No. 10 was used as a probe for the aforementioned rat orthologous gene of the potassium channel described in Sequence No. 6. It was found that this potassium channel was strongly expressed in neurons of the cerebral cortex.

EXAMPLE 4

Induction of the Expression of Novel Potassium Channel Protein

In order to detect channel activity of the novel potassium channel protein, expression of the protein was induced in an animal cell. As the cell, L929 cell which does not generate current by intrinsic channel through changes in the membrane potential was used. Transfection of the cell was carried out by lipofectAMINE method using pME-E1 plasmid or pME-E2 plasmid.

EXAMPLE 5

Detection of Channel Activity of Novel Potassium Channel Protein

The transfected cell was voltage-clamped and whole-cell current was measured using the whole-cell voltage-clamp method. A solution containing 140 mM NaCl, 5.4 mM KCl, 2 mM CaCl$_2$, 0.8 mM MgCl$_2$, 15 mM glucose and 10 mM HEPES-Na (pH=7.4) was used as the extracellular solution, and a solution containing 125 mM KCl, 1 mM CaCl$_2$, 2 mM MgCl$_2$, 11 mM EGTA and 10 mM HEPES-K (pH=7.2) was used as the intracellular solution.

Figure 5:
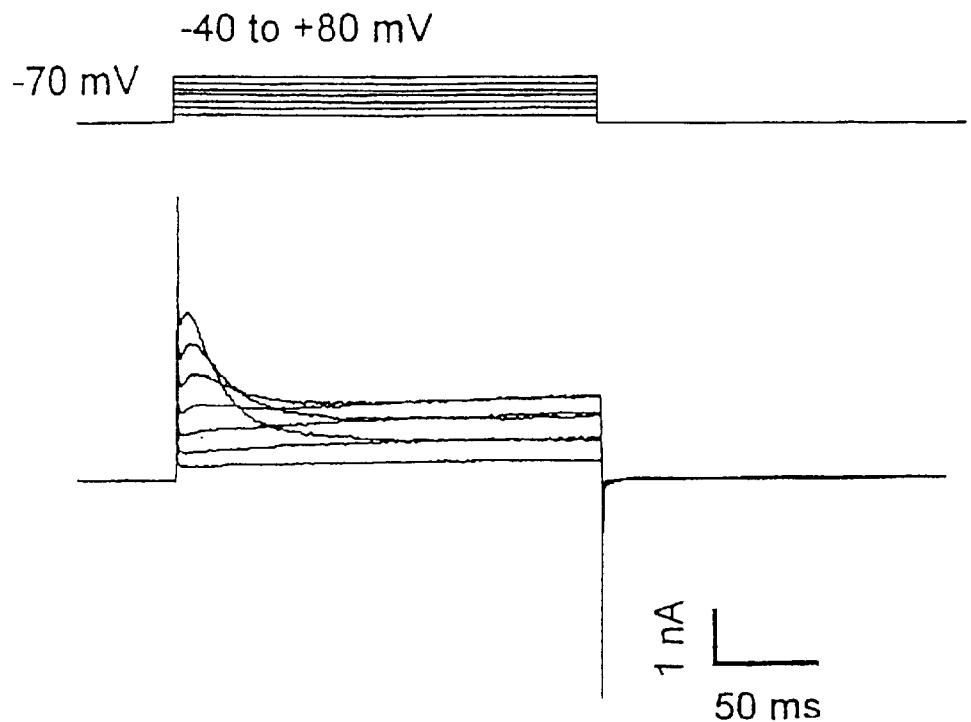
FIG. 5 shows results of the detection of the channel activity of potassium channel (Sequence No. 2) by depolarization stimulus.
Figure 6:
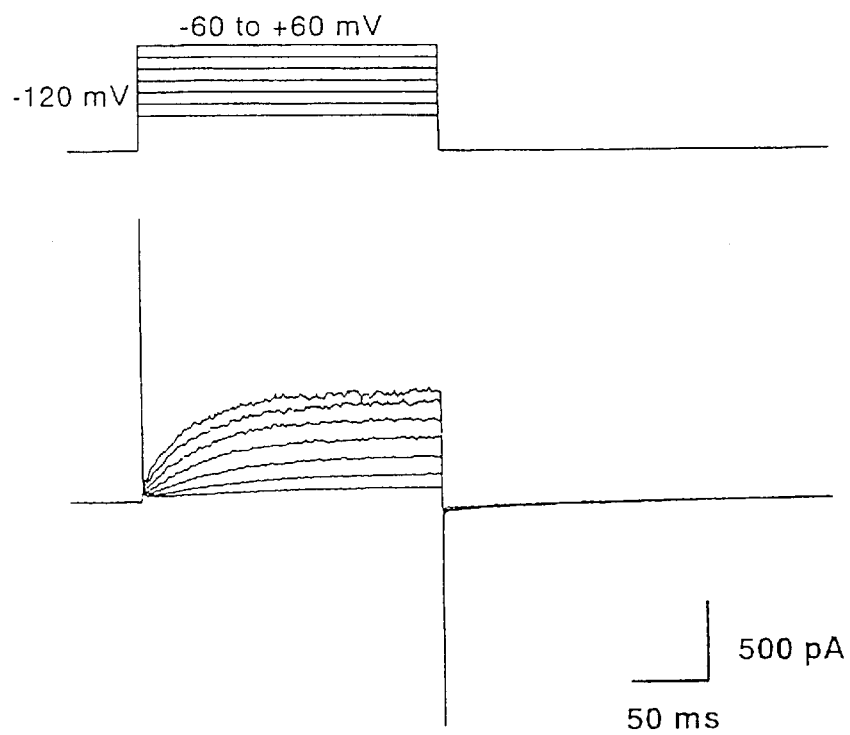
FIG. 6 shows results of the detection of the channel activity of po tassium channel (Sequence No. 6) by depolarization stimulus.

The cell transfected with pME-E1 was depolarized to voltages between −40 mV and +80 mV at 20 mV intervals for 200 msec from the holding potential of −70 mV (FIG. 5), or the cells transfected with pME-E2 was depolarized to voltages between −60 mV and +60 mV at 20 mV intervals for 200 msec from the holding potential of −120 mV (FIG. 6). As a result, distinctive outward current was induced in both cells. It was found from this result that both of the protein shown in Sequence No. 2 and the protein shown in Sequence No. 6 are voltage-dependent channels.

EXAMPLE 6

Selectivity of K$^+$ion by Novel Potassium Channel Protein

Figure 7:
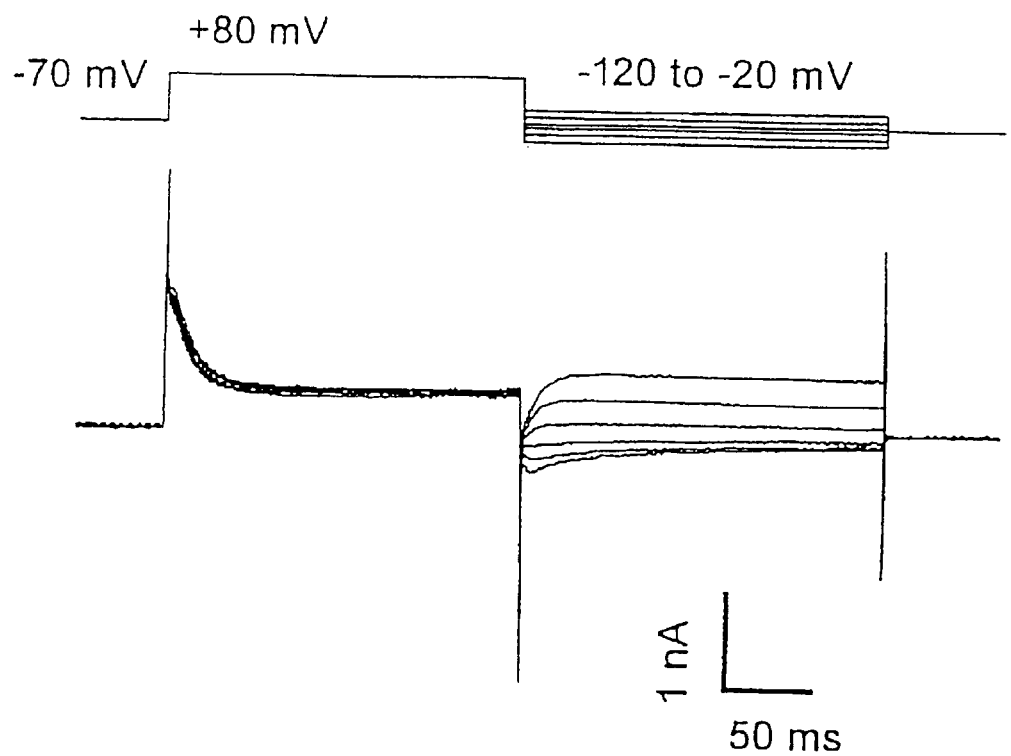
FIG. 7 shows tail current of the potassium channel shown in Sequence No. 2.

In order to examine selectivity of K$^+$ion by the potassium channel shown in Sequence No. 2, tail current was measured. The current was examined by a method similar to Example 5. Based on the tail current (activation of the channel by depolarization stimulus of +80 mV for 200 msec from the holding potential of −70 mV and then re-polarization to voltages between −120 mV and −20 mV at 20 mV intervals), the reversal potential in this solution was found to be −80 mV (FIG. 7). Since this value almost coincided with the equilibrium potential of K$^+$obtained by the formula of Nernst (−87 mV, 25° C.; [K]out=5.4 mM, [K]in=158 mM), this channel was considered to have large selectivity for K$^+$ion.

Figure 8:
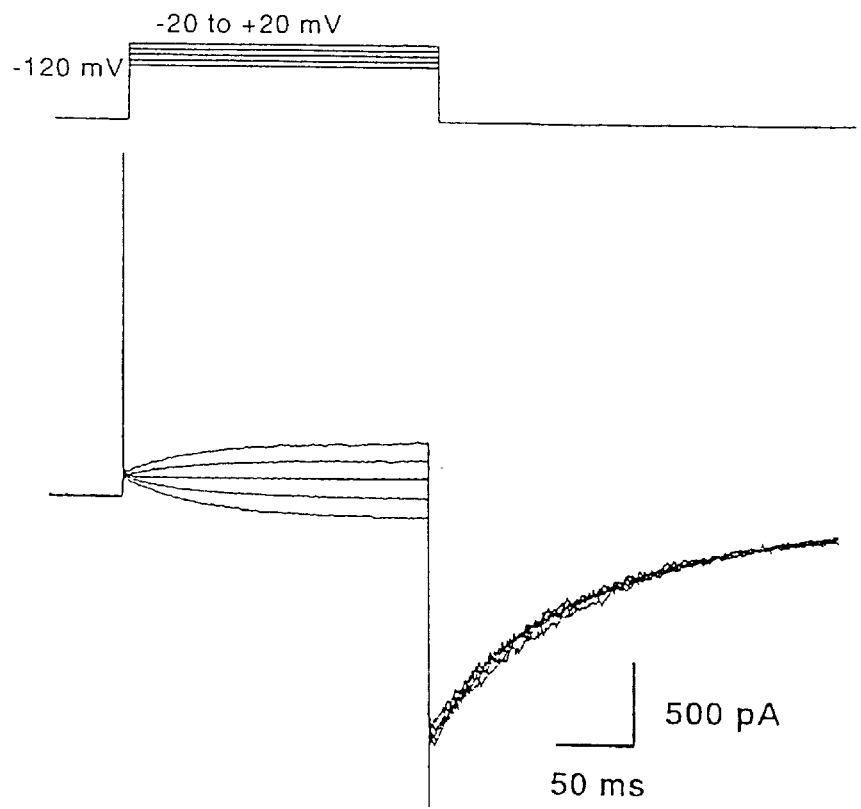
FIG. 8 shows current response of the pot assium channel shown in Sequence No. 6 in high potassium extracellular liquid.

An extracellular solution containing 155 mM KCl, 4.5 mM N-methyl-D-glucamine, 2 mM CaCl$_2$, 10 mM glucose and 10 mM HEPES (pH=7.4) was used for the examination of K$^+$selectivity of the potassium channel shown in Sequence No. 6. Other conditions were examined by a method similar to Example 5. When depolarization stimulus (between −20 mV and +20 mV at 10 mV intervals for 200 msec from the holding potential of −120 mV) was carried out, the current response was reversed at 0 mV (FIG. 8). It was estimated from this result that the reverse potential was approximately 0 mV. Since this value almost coincided with the equilibrium potential of K$^+$obtained by the formula of Nernst (−5 mV, 25° C.; [K]out=155 mM, [K]in=158 mM), and outward current was induced in Example 5, this channel was considered to have large selectivity for K$^+$ion.

Industrial Applicability

A novel potassium channel protein expressed exclusively in the brain, a gene encoding this protein, a vector containing this gene, a host cell containing this vector and a method for producing this potassium channel protein were provided by the present invention.

Also, there was provided a method for the screening of new medicaments, particularly new therapeutic agents for central nervous system disorders, in which compounds and peptides capable of modifying activity of the potassium channel protein are screened by allowing the potassium channel protein of the present invention to contact with agents to be tested.

For example, among tissues in which the potassium channel of the present invention shown in Sequence No. 2 was expressed as the result of Example 3, hippocampus is a region where its relationship with memory and learning is strongly suggested (Lavitan, I. B. and Kaczmarek, L. K. (1991), *The Neuron: Cell and Molecular Biology*, Oxford University Press, New York, N.Y.). Particularly, granule cells of the dentate gyrus and pyramidal cells of the CA1 and CA3 fields in which expression of the potassium channel was confirmed form a neural circuit, and various memory inputs are transmitted from the granule cells of the dentate gyrus to pyramidal cells of the CA3 field via pyramidal cells of the CA1 field, mediated by an excitatory synapse which uses glutamic acid as a neurotransmitter. It is considered that long-term changes in the efficiency of synaptic transmission observed in respective synapse, such as long-term increase and long-term repression, are deeply concerned in memory and learning. These long-term changes are controlled by the excitation frequency and excitation strength of nerve cells, and voltage-dependent potassium channels generally have a possibility of being able to control excitability of neurons, so that the potassium channel protein of the present invention which is a voltage-dependent potassium channel has a possibility that it is concerned in the formation of memory and learning via the excitability control of neurons.

Regarding the medicament which contains a compound or peptide capable of specifically modifying activity of the potassium channel protein of the present invention as its active ingredient, its usefulness is expected for example as a therapeutic agent for central nervous system disorders such as dementia, cerebral ischemic disorders and epilepsy, which acts central nervous system-specifically and has less side effects.

What is claimed is:

1. An isolated potassium channel protein, which comprises an amino acid sequence selected from the group consisting of SEQ ID NO: 2 and SEQ ID NO: 6, and which is expressed exclusively in the brain.

2. An isolated polynucleotide molecule which comprises a nucleotide sequence encoding an amino acid sequence selected from the group consisting of SEQ ID NO: 2 and SEQ ID NO: 6.

3. An isolated polynucleotide molecule which comprises a nucleotide sequence selected from the group consisting of the 6th to 3257th nucleotide sequence of SEQ ID NO. 1 and, the 4th to 3057th nucleotide sequence of SEQ ID NO: 5, and a nucleotide sequence which is degenerate with respect to said nucleotide molecule.

4. An isolated mammalian polynucleotide molecule that hybridizes with a nucleotide sequence of SEQ ID NO: 1 or SEQ ID NO: 5 under stringent conditions and encodes a brain specific potassium channel protein, wherein a sampie is washed twice in 2×SSC containing 0.1% SDS and then subjected to a third washing step, wherein said third washing step is carried out in a solution selected from the group consisting of 0.5×SSC containing 0.1% SDS, 0.2×SSC containing 0.1% SDS, and 0.1×SSC containing 0.1% SDS.

5. A vector which comprises the polynucleotide molecule according to claim 4.

6. A vector which comprises the polynucleotide molecule according to claim 2.

7. A vector which comprises the polynucleotide molecule according to claim 3.

8. A host cell which comprises the vector according to any one of claims 5, 6 and 7.

9. A method for producing a potassium channel protein comprising expressing the protein in a host cell or on a host cell surface containing a vector according to any one of claims 5, 6 and 7.

10. An isolated potassium channel protein which is produced in a host cell or on a host cell surface containing a vector according to claim 5, wherein the protein is encoded by the vector.

* * * * *

UNITED STATES PATENT AND TRADEMARK OFFICE
CERTIFICATE OF CORRECTION

PATENT NO. : 6,326,168 B1
DATED : December 4, 2001
INVENTOR(S) : Miyake, Akira, Mochizuki, Shinobu, Yokoi and Hiromichi It is certified that error appears in the above-identified patent and that said Letters Patent is hereby corrected as shown below:

<u>Column 49,</u>
Line 44, delete "sampie" and insert therefore -- sample --.

Signed and Sealed this

Eighteenth Day of June, 2002

Attest:

Attesting Officer

JAMES E. ROGAN
*Director of the United States Patent and Trademark Office*

SEQUENCE LISTING

```
<160> NUMBER OF SEQ ID NOS:  12

<210> SEQ ID NO 1
<211> LENGTH: 3323
<212> TYPE: DNA
<213> ORGANISM: Homo sapiens
<220> FEATURE:
<221> NAME/KEY: CDS
<222> LOCATION: (6)..(3257)

<400> SEQUENCE: 1 ctaag atg ccg gcc atg cgg ggc ctc ctg gcg cct cag aac acc ttc ctg      50
```

-continued

```
    Met Pro Ala Met Arg Gly Leu Leu Ala Pro Gln Asn Thr Phe Leu
     1               5                  10                  15 gac acc atc gct acg cgc ttc gac ggc acg cac agt aac ttc gtg ctg      98
Asp Thr Ile Ala Thr Arg Phe Asp Gly Thr His Ser Asn Phe Val Leu
                 20                  25                  30 ggc aac gcc cag gtg gcg ggg ctc ttc ccc gtg gtc tac tgc tct gat     146
Gly Asn Ala Gln Val Ala Gly Leu Phe Pro Val Val Tyr Cys Ser Asp
             35                  40                  45 ggc ttc tgt gac ctc acg ggc ttc tcc cgg gct gag gtc atg cag cgg     194
Gly Phe Cys Asp Leu Thr Gly Phe Ser Arg Ala Glu Val Met Gln Arg
         50                  55                  60 ggc tgt gcc tgc tcc ttc ctt tat ggg cca gac acc agt gag ctc gtc     242
Gly Cys Ala Cys Ser Phe Leu Tyr Gly Pro Asp Thr Ser Glu Leu Val
     65                  70                  75 cgc caa cag atc cgc aag gcc ctg gac gag cac aag gag ttc aag gct     290
Arg Gln Gln Ile Arg Lys Ala Leu Asp Glu His Lys Glu Phe Lys Ala
 80                  85                  90                  95 gag ctg atc ctg tac cgg aag agc ggg ctc ccg ttc tgg tgt ctc ctg     338
Glu Leu Ile Leu Tyr Arg Lys Ser Gly Leu Pro Phe Trp Cys Leu Leu
                100                 105                 110 gat gtg ata ccc ata aag aat gag aaa ggg gag gtg gct ctc ttc cta     386
Asp Val Ile Pro Ile Lys Asn Glu Lys Gly Glu Val Ala Leu Phe Leu
            115                 120                 125 gtc tct cac aag gac atc agc gaa acc aag aac cga ggg ggc ccc gac     434
Val Ser His Lys Asp Ile Ser Glu Thr Lys Asn Arg Gly Gly Pro Asp
        130                 135                 140 aga tgg aag gag aca ggt ggt ggc cgg cgc cga tat ggc cgg gca cga     482
Arg Trp Lys Glu Thr Gly Gly Gly Arg Arg Arg Tyr Gly Arg Ala Arg
    145                 150                 155 tcc aaa ggc ttc aat gcc aac cgg cgg cgg agc cgg gcc gtg ctc tac     530
Ser Lys Gly Phe Asn Ala Asn Arg Arg Arg Ser Arg Ala Val Leu Tyr
160                 165                 170                 175 cac ctg tcc ggg cac ctg cag aag cag ccc aag ggc aag cac aag ctc     578
His Leu Ser Gly His Leu Gln Lys Gln Pro Lys Gly Lys His Lys Leu
                180                 185                 190 aat aag ggg gtg ttt ggg gag aaa cca aac ttg cct gag tac aaa gta     626
Asn Lys Gly Val Phe Gly Glu Lys Pro Asn Leu Pro Glu Tyr Lys Val
            195                 200                 205 gcc gcc atc cgg aag tcg ccc ttc atc ctg ttg cac tgt ggg gca ctg     674
Ala Ala Ile Arg Lys Ser Pro Phe Ile Leu Leu His Cys Gly Ala Leu
        210                 215                 220 aga gcc acc tgg gat ggc ttc atc ctg ctc gcc aca ctc tat gtg gct     722
Arg Ala Thr Trp Asp Gly Phe Ile Leu Leu Ala Thr Leu Tyr Val Ala
    225                 230                 235 gtc act gtg ccc tac agc gtg tgt gtg agc aca gca cgg gag ccc agt     770
Val Thr Val Pro Tyr Ser Val Cys Val Ser Thr Ala Arg Glu Pro Ser
240                 245                 250                 255 gcc gcc cgc ggc ccg ccc agc gtc tgt gac ctg gcc gtg gag gtc ctc     818
Ala Ala Arg Gly Pro Pro Ser Val Cys Asp Leu Ala Val Glu Val Leu
                260                 265                 270 ttc atc ctt gac att gtg ctg aat ttc cgt acc aca ttc gtg tcc aag     866
Phe Ile Leu Asp Ile Val Leu Asn Phe Arg Thr Thr Phe Val Ser Lys
            275                 280                 285 tcg ggc cag gtg gtg ttt gcc cca aag tcc att tgc ctc cac tac gtc     914
Ser Gly Gln Val Val Phe Ala Pro Lys Ser Ile Cys Leu His Tyr Val
        290                 295                 300 acc acc tgg ttc ctg ctg gat gtc atc gca gcg ctg ccc ttt gac ctg     962
Thr Thr Trp Phe Leu Leu Asp Val Ile Ala Ala Leu Pro Phe Asp Leu
    305                 310                 315
```

```
cta cat gcc ttc aag gtc aac gtg tac ttc ggg gcc cat ctg ctg aag      1010
Leu His Ala Phe Lys Val Asn Val Tyr Phe Gly Ala His Leu Leu Lys
320             325                 330                 335 acg gtg cgc ctg ctg cgc ctg ctg cgc ctg ctt ccg cgg ctg gac cgg      1058
Thr Val Arg Leu Leu Arg Leu Leu Arg Leu Leu Pro Arg Leu Asp Arg
                340                 345                 350 tac tcg cag tac agc gcc gtg gtg ctg aca ctg ctc atg gcc gtg ttc      1106
Tyr Ser Gln Tyr Ser Ala Val Val Leu Thr Leu Leu Met Ala Val Phe
            355                 360                 365 gcc ctg ctc gcg cac tgg gtc gcc tgc gtc tgg ttt tac att ggc cag      1154
Ala Leu Leu Ala His Trp Val Ala Cys Val Trp Phe Tyr Ile Gly Gln
        370                 375                 380 cgg gag atc gag agc agc gaa tcc gag ctg cct gag att ggc tgg ctg      1202
Arg Glu Ile Glu Ser Ser Glu Ser Glu Leu Pro Glu Ile Gly Trp Leu
    385                 390                 395 cag gag ctg gcc cgc cga ctg gag act ccc tac tac ctg gtg ggc cgg      1250
Gln Glu Leu Ala Arg Arg Leu Glu Thr Pro Tyr Tyr Leu Val Gly Arg
400                 405                 410                 415 agg cca gct gga ggg aac agc tcc ggc cag agt gac aac tgc agc agc      1298
Arg Pro Ala Gly Gly Asn Ser Ser Gly Gln Ser Asp Asn Cys Ser Ser
                420                 425                 430 agc agc gag gcc aac ggg acg ggg ctg gag ctg ctg ggc ggc ccg tcg      1346
Ser Ser Glu Ala Asn Gly Thr Gly Leu Glu Leu Leu Gly Gly Pro Ser
            435                 440                 445 ctg cgc agc gcc tac atc acc tcc ctc tac ttc gca ctc agc agc ctc      1394
Leu Arg Ser Ala Tyr Ile Thr Ser Leu Tyr Phe Ala Leu Ser Ser Leu
        450                 455                 460 acc agc gtg ggc ttc ggc aac gtg tcc gcc aac acg gac acc gag aag      1442
Thr Ser Val Gly Phe Gly Asn Val Ser Ala Asn Thr Asp Thr Glu Lys
    465                 470                 475 atc ttc tcc atc tgc acc atg ctc atc ggc gcc ctg atg cac gcg gtg      1490
Ile Phe Ser Ile Cys Thr Met Leu Ile Gly Ala Leu Met His Ala Val
480                 485                 490                 495 gtg ttt ggg aac gtg acg gcc atc atc cag cgc atg tac gcc cgc cgc      1538
Val Phe Gly Asn Val Thr Ala Ile Ile Gln Arg Met Tyr Ala Arg Arg
                500                 505                 510 ttt ctg tac cac agc cgc acg cgc gac ctg cgc gac tac atc cgc atc      1586
Phe Leu Tyr His Ser Arg Thr Arg Asp Leu Arg Asp Tyr Ile Arg Ile
            515                 520                 525 cac cgt atc ccc aag ccc ctc aag cag cgc atg ctg gag tac ttc cag      1634
His Arg Ile Pro Lys Pro Leu Lys Gln Arg Met Leu Glu Tyr Phe Gln
        530                 535                 540 gcc acc tgg gcg gtg aac aat ggc atc gac acc acc gag ctg ctg cag      1682
Ala Thr Trp Ala Val Asn Asn Gly Ile Asp Thr Thr Glu Leu Leu Gln
    545                 550                 555 agc ctc cct gac gag ctg cgc gca gac atc gcc atg cac ctg cac aag      1730
Ser Leu Pro Asp Glu Leu Arg Ala Asp Ile Ala Met His Leu His Lys
560                 565                 570                 575 gag gtc ctg cag ctg cca ctg ttt gag gcg gcc agc cgc ggc tgc ctg      1778
Glu Val Leu Gln Leu Pro Leu Phe Glu Ala Ala Ser Arg Gly Cys Leu
                580                 585                 590 cgg gca ctg tct ctg gcc ctg cgg ccc gcc ttc tgc acg ccg ggc gag      1826
Arg Ala Leu Ser Leu Ala Leu Arg Pro Ala Phe Cys Thr Pro Gly Glu
            595                 600                 605 tac ctc atc cac caa ggc gat gcc ctg cag gcc ctc tac ttt gtc tgc      1874
Tyr Leu Ile His Gln Gly Asp Ala Leu Gln Ala Leu Tyr Phe Val Cys
        610                 615                 620 tct ggc tcc atg gag gtg ctc aag ggt ggc acc gtg ctc gcc atc cta      1922
Ser Gly Ser Met Glu Val Leu Lys Gly Gly Thr Val Leu Ala Ile Leu
    625                 630                 635
```

```
ggg aag ggc gac ctg atc ggc tgt gag ctg ccc cgg cgg gag cag gtg      1970
Gly Lys Gly Asp Leu Ile Gly Cys Glu Leu Pro Arg Arg Glu Gln Val
640             645                 650                 655 gta aag gcc aat gcc gac gtg aag ggg ctg acg tac tgc gtc ctg cag      2018
Val Lys Ala Asn Ala Asp Val Lys Gly Leu Thr Tyr Cys Val Leu Gln
            660                 665                 670 tgt ctg cag ctg gct ggc ctg cac gac agc ctt gcg ctg tac ccc gag      2066
Cys Leu Gln Leu Ala Gly Leu His Asp Ser Leu Ala Leu Tyr Pro Glu
        675                 680                 685 ttt gcc ccg cgc ttc agt cgt ggc ctc cga ggg gag ctc agc tac aac      2114
Phe Ala Pro Arg Phe Ser Arg Gly Leu Arg Gly Glu Leu Ser Tyr Asn
    690                 695                 700 ctg ggt gct ggg gga ggc tct gca gag gtg gac acc agc tcc ctg agc      2162
Leu Gly Ala Gly Gly Gly Ser Ala Glu Val Asp Thr Ser Ser Leu Ser
705                 710                 715 ggc gac aat acc ctt atg tcc acg ctg gag gag aag gag aca gat ggg      2210
Gly Asp Asn Thr Leu Met Ser Thr Leu Glu Glu Lys Glu Thr Asp Gly
720                 725                 730                 735 gag cag ggc ccc acg gtc tcc cca gcc cca gct gat gag ccc tcc agc      2258
Glu Gln Gly Pro Thr Val Ser Pro Ala Pro Ala Asp Glu Pro Ser Ser
                740                 745                 750 ccc ctg ctg tcc cct ggc tgc acc tcc tca tcc tca gct gcc aag ctg      2306
Pro Leu Leu Ser Pro Gly Cys Thr Ser Ser Ser Ser Ala Ala Lys Leu
            755                 760                 765 cta tcc cca cgt cga aca gca ccc cgg cct cgt cta ggt ggc aga ggg      2354
Leu Ser Pro Arg Arg Thr Ala Pro Arg Pro Arg Leu Gly Gly Arg Gly
        770                 775                 780 agg cca ggc agg gca ggg gct ttg aag gct gag gct ggc ccc tct gct      2402
Arg Pro Gly Arg Ala Gly Ala Leu Lys Ala Glu Ala Gly Pro Ser Ala
785                 790                 795 ccc cca cgg gcc cta gag ggg cta cgg ctg ccc ccc atg cca tgg aat      2450
Pro Pro Arg Ala Leu Glu Gly Leu Arg Leu Pro Pro Met Pro Trp Asn
800                 805                 810                 815 gtg ccc cca gat ctg agc ccc agg gta gta gat ggc att gaa gac ggc      2498
Val Pro Pro Asp Leu Ser Pro Arg Val Val Asp Gly Ile Glu Asp Gly
                820                 825                 830 tgt ggc tcg gac cag ccc aag ttc tct ttc cgc gtg ggc cag tct ggc      2546
Cys Gly Ser Asp Gln Pro Lys Phe Ser Phe Arg Val Gly Gln Ser Gly
            835                 840                 845 ccg gaa tgt agc agc agc ccc tcc cct gga cca gag agc ggc ctg ctc      2594
Pro Glu Cys Ser Ser Ser Pro Ser Pro Gly Pro Glu Ser Gly Leu Leu
        850                 855                 860 act gtt ccc cat ggg ccc agc gag gca agg aac aca gac aca ctg gac      2642
Thr Val Pro His Gly Pro Ser Glu Ala Arg Asn Thr Asp Thr Leu Asp
865                 870                 875 aag ctt cgg cag gcg gtg aca gag ctg tca gag cag gtg ctg cag atg      2690
Lys Leu Arg Gln Ala Val Thr Glu Leu Ser Glu Gln Val Leu Gln Met
880                 885                 890                 895 cgg gaa gga ctg cag tca ctt cgc cag gct gtg cag ctt gtc ctg gcg      2738
Arg Glu Gly Leu Gln Ser Leu Arg Gln Ala Val Gln Leu Val Leu Ala
                900                 905                 910 ccc cac agg gag ggt ccg tgc cct cgg gca tcg gga gag ggg ccg tgc      2786
Pro His Arg Glu Gly Pro Cys Pro Arg Ala Ser Gly Glu Gly Pro Cys
            915                 920                 925 cca gcc agc acc tcc ggg ctt ctg cag cct ctg tgt gtg gac act ggg      2834
Pro Ala Ser Thr Ser Gly Leu Leu Gln Pro Leu Cys Val Asp Thr Gly
        930                 935                 940 gca tcc tcc tac tgc ctg cag ccc cca gct ggc tct gtc ttg agt ggg      2882
Ala Ser Ser Tyr Cys Leu Gln Pro Pro Ala Gly Ser Val Leu Ser Gly
```

-continued

```
              945                 950                 955
act tgg ccc cac cct cgt ccg ggg cct cct ccc ctc atg gca ccc tgg     2930
Thr Trp Pro His Pro Arg Pro Gly Pro Pro Pro Leu Met Ala Pro Trp
960                 965                 970                 975 ccc tgg ggt ccc cca gcg tct cag agc tcc ccc tgg cct cga gcc aca     2978
Pro Trp Gly Pro Pro Ala Ser Gln Ser Ser Pro Trp Pro Arg Ala Thr
            980                 985                 990 gct ttc tgg acc tcc acc tca gac tca gag ccc cct gcc tca gga gac     3026
Ala Phe Trp Thr Ser Thr Ser Asp Ser Glu Pro Pro Ala Ser Gly Asp
        995                 1000                1005 ctc tgc tct gag ccc agc acc cct gcc tcc cct cct cct tct gag gaa     3074
Leu Cys Ser Glu Pro Ser Thr Pro Ala Ser Pro Pro Pro Ser Glu Glu
        1010                1015                1020 ggg gct agg act ggg ccc gca gag cct gtg agc cag gct gag gct acc     3122
Gly Ala Arg Thr Gly Pro Ala Glu Pro Val Ser Gln Ala Glu Ala Thr
    1025                1030                1035 agc act gga gag ccc cca cca ggg tca ggg ggc ctg gcc ttg ccc tgg     3170
Ser Thr Gly Glu Pro Pro Pro Gly Ser Gly Gly Leu Ala Leu Pro Trp
1040                1045                1050                1055 gac ccc cac agc ctg gag atg gtg ctt att ggc tgc cat ggc tct ggc     3218
Asp Pro His Ser Leu Glu Met Val Leu Ile Gly Cys His Gly Ser Gly
            1060                1065                1070 aca gtc cag tgg acc cag gaa gaa ggc aca ggg gtc tga gtaccagccc     3267
Thr Val Gln Trp Thr Gln Glu Glu Gly Thr Gly Val
        1075                1080 tagaactcag cgttgccagg tgtgctgcca tctgctgttc ggcccaacct cagagt       3323
```

<210> SEQ ID NO 2
<211> LENGTH: 1083
<212> TYPE: PRT
<213> ORGANISM: Homo sapiens

<400> SEQUENCE: 2

```
Met Pro Ala Met Arg Gly Leu Leu Ala Pro Gln Asn Thr Phe Leu Asp
 1               5                  10                  15

Thr Ile Ala Thr Arg Phe Asp Gly Thr His Ser Asn Phe Val Leu Gly
            20                  25                  30

Asn Ala Gln Val Ala Gly Leu Phe Pro Val Val Tyr Cys Ser Asp Gly
        35                  40                  45

Phe Cys Asp Leu Thr Gly Phe Ser Arg Ala Glu Val Met Gln Arg Gly
    50                  55                  60

Cys Ala Cys Ser Phe Leu Tyr Gly Pro Asp Thr Ser Glu Leu Val Arg
65                  70                  75                  80

Gln Gln Ile Arg Lys Ala Leu Asp Glu His Lys Glu Phe Lys Ala Glu
                85                  90                  95

Leu Ile Leu Tyr Arg Lys Ser Gly Leu Pro Phe Trp Cys Leu Leu Asp
            100                 105                 110

Val Ile Pro Ile Lys Asn Glu Lys Gly Glu Val Ala Leu Phe Leu Val
        115                 120                 125

Ser His Lys Asp Ile Ser Glu Thr Lys Asn Arg Gly Gly Pro Asp Arg
    130                 135                 140

Trp Lys Glu Thr Gly Gly Gly Arg Arg Arg Tyr Gly Arg Ala Arg Ser
145                 150                 155                 160

Lys Gly Phe Asn Ala Asn Arg Arg Arg Ser Arg Ala Val Leu Tyr His
                165                 170                 175

Leu Ser Gly His Leu Gln Lys Gln Pro Lys Gly Lys His Lys Leu Asn
            180                 185                 190
```

-continued

Lys Gly Val Phe Gly Glu Lys Pro Asn Leu Pro Glu Tyr Lys Val Ala
        195                 200                 205

Ala Ile Arg Lys Ser Pro Phe Ile Leu Leu His Cys Gly Ala Leu Arg
    210                 215                 220

Ala Thr Trp Asp Gly Phe Ile Leu Leu Ala Thr Leu Tyr Val Ala Val
225                 230                 235                 240

Thr Val Pro Tyr Ser Val Cys Val Ser Thr Ala Arg Glu Pro Ser Ala
                245                 250                 255

Ala Arg Gly Pro Pro Ser Val Cys Asp Leu Ala Val Glu Val Leu Phe
            260                 265                 270

Ile Leu Asp Ile Val Leu Asn Phe Arg Thr Thr Phe Val Ser Lys Ser
        275                 280                 285

Gly Gln Val Val Phe Ala Pro Lys Ser Ile Cys Leu His Tyr Val Thr
    290                 295                 300

Thr Trp Phe Leu Leu Asp Val Ile Ala Ala Leu Pro Phe Asp Leu Leu
305                 310                 315                 320

His Ala Phe Lys Val Asn Val Tyr Phe Gly Ala His Leu Leu Lys Thr
                325                 330                 335

Val Arg Leu Leu Arg Leu Leu Arg Leu Leu Pro Arg Leu Asp Arg Tyr
            340                 345                 350

Ser Gln Tyr Ser Ala Val Val Leu Thr Leu Leu Met Ala Val Phe Ala
        355                 360                 365

Leu Leu Ala His Trp Val Ala Cys Val Trp Phe Tyr Ile Gly Gln Arg
    370                 375                 380

Glu Ile Glu Ser Glu Ser Glu Leu Pro Glu Ile Gly Trp Leu Gln
385                 390                 395                 400

Glu Leu Ala Arg Arg Leu Glu Thr Pro Tyr Tyr Leu Val Gly Arg Arg
                405                 410                 415

Pro Ala Gly Gly Asn Ser Ser Gly Gln Ser Asp Asn Cys Ser Ser Ser
            420                 425                 430

Ser Glu Ala Asn Gly Thr Gly Leu Glu Leu Leu Gly Gly Pro Ser Leu
        435                 440                 445

Arg Ser Ala Tyr Ile Thr Ser Leu Tyr Phe Ala Leu Ser Ser Leu Thr
    450                 455                 460

Ser Val Gly Phe Gly Asn Val Ser Ala Asn Thr Asp Thr Glu Lys Ile
465                 470                 475                 480

Phe Ser Ile Cys Thr Met Leu Ile Gly Ala Leu Met His Ala Val Val
                485                 490                 495

Phe Gly Asn Val Thr Ala Ile Ile Gln Arg Met Tyr Ala Arg Arg Phe
            500                 505                 510

Leu Tyr His Ser Arg Thr Arg Asp Leu Arg Asp Tyr Ile Arg Ile His
        515                 520                 525

Arg Ile Pro Lys Pro Leu Lys Gln Arg Met Leu Glu Tyr Phe Gln Ala
    530                 535                 540

Thr Trp Ala Val Asn Asn Gly Ile Asp Thr Thr Glu Leu Leu Gln Ser
545                 550                 555                 560

Leu Pro Asp Glu Leu Arg Ala Asp Ile Ala Met His Leu His Lys Glu
                565                 570                 575

Val Leu Gln Leu Pro Leu Phe Glu Ala Ser Arg Gly Cys Leu Arg
            580                 585                 590

Ala Leu Ser Leu Ala Leu Arg Pro Ala Phe Cys Thr Pro Gly Glu Tyr
        595                 600                 605

```
Leu Ile His Gln Gly Asp Ala Leu Gln Ala Leu Tyr Phe Val Cys Ser
    610                 615                 620

Gly Ser Met Glu Val Leu Lys Gly Gly Thr Val Leu Ala Ile Leu Gly
625                 630                 635                 640

Lys Gly Asp Leu Ile Gly Cys Glu Leu Pro Arg Arg Glu Gln Val Val
                645                 650                 655

Lys Ala Asn Ala Asp Val Lys Gly Leu Thr Tyr Cys Val Leu Gln Cys
            660                 665                 670

Leu Gln Leu Ala Gly Leu His Asp Ser Leu Ala Leu Tyr Pro Glu Phe
        675                 680                 685

Ala Pro Arg Phe Ser Arg Gly Leu Arg Gly Glu Leu Ser Tyr Asn Leu
    690                 695                 700

Gly Ala Gly Gly Ser Ala Glu Val Asp Thr Ser Ser Leu Ser Gly
705                 710                 715                 720

Asp Asn Thr Leu Met Ser Thr Leu Glu Glu Lys Glu Thr Asp Gly Glu
                725                 730                 735

Gln Gly Pro Thr Val Ser Pro Ala Pro Ala Asp Glu Pro Ser Ser Pro
            740                 745                 750

Leu Leu Ser Pro Gly Cys Thr Ser Ser Ser Ala Ala Lys Leu Leu
        755                 760                 765

Ser Pro Arg Arg Thr Ala Pro Arg Pro Leu Gly Gly Arg Gly Arg
    770                 775                 780

Pro Gly Arg Ala Gly Ala Leu Lys Ala Glu Ala Gly Pro Ser Ala Pro
785                 790                 795                 800

Pro Arg Ala Leu Glu Gly Leu Arg Leu Pro Pro Met Pro Trp Asn Val
                805                 810                 815

Pro Pro Asp Leu Ser Pro Arg Val Val Asp Gly Ile Glu Asp Gly Cys
            820                 825                 830

Gly Ser Asp Gln Pro Lys Phe Ser Phe Arg Val Gly Gln Ser Gly Pro
        835                 840                 845

Glu Cys Ser Ser Pro Ser Pro Gly Pro Glu Ser Gly Leu Leu Thr
    850                 855                 860

Val Pro His Gly Pro Ser Glu Ala Arg Asn Thr Asp Thr Leu Asp Lys
865                 870                 875                 880

Leu Arg Gln Ala Val Thr Glu Leu Ser Glu Gln Val Leu Gln Met Arg
                885                 890                 895

Glu Gly Leu Gln Ser Leu Arg Gln Ala Val Gln Leu Val Leu Ala Pro
            900                 905                 910

His Arg Glu Gly Pro Cys Pro Arg Ala Ser Gly Glu Gly Pro Cys Pro
        915                 920                 925

Ala Ser Thr Ser Gly Leu Leu Gln Pro Leu Cys Val Asp Thr Gly Ala
    930                 935                 940

Ser Ser Tyr Cys Leu Gln Pro Ala Gly Ser Val Leu Ser Gly Thr
945                 950                 955                 960

Trp Pro His Pro Arg Pro Gly Pro Pro Leu Met Ala Pro Trp Pro
                965                 970                 975

Trp Gly Pro Pro Ala Ser Gln Ser Ser Pro Trp Pro Arg Ala Thr Ala
            980                 985                 990

Phe Trp Thr Ser Thr Ser Asp Ser Glu Pro Pro Ala Ser Gly Asp Leu
        995                 1000                1005

Cys Ser Glu Pro Ser Thr Pro Ala Ser Pro Pro Ser Glu Glu Gly
    1010                1015                1020

Ala Arg Thr Gly Pro Ala Glu Pro Val Ser Gln Ala Glu Ala Thr Ser
```

```
                        1025                1030                1035                1040
                    Thr Gly Glu Pro Pro Pro Gly Ser Gly Gly Leu Ala Leu Pro Trp Asp
                                        1045                1050                1055

Pro His Ser Leu Glu Met Val Leu Ile Gly Cys His Gly Ser Gly Thr
                                1060                1065                1070

Val Gln Trp Thr Gln Glu Glu Gly Thr Gly Val
                            1075                1080

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence:Primer

<400> SEQUENCE: 3
ggaattccct aagatgccgg ccatgc                                                26

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:Primer

<400> SEQUENCE: 4
gctctagagc actctgaggt tgggccgaac                                            30

<210> SEQ ID NO 5
<211> LENGTH: 3064
<212> TYPE: DNA
<213> ORGANISM: Homo sapiens
<220> FEATURE:
<221> NAME/KEY: CDS
<222> LOCATION: (4)..(3057)

<400> SEQUENCE: 5 gcc atg ccg gtc atg aag ggg ttg ctg gcc ccg caa aac acc ttc ctg            48
    Met Pro Val Met Lys Gly Leu Leu Ala Pro Gln Asn Thr Phe Leu
     1               5                  10                  15 gac acc atc gcc acc cgt ttt gac gga acg cac agc aac ttc ctg ctg            96
Asp Thr Ile Ala Thr Arg Phe Asp Gly Thr His Ser Asn Phe Leu Leu
                 20                  25                  30 gcc aac gca cag ggc aca cgg ggc ttt ccc atc gtc tac tgc tcc gac           144
Ala Asn Ala Gln Gly Thr Arg Gly Phe Pro Ile Val Tyr Cys Ser Asp
             35                  40                  45 ggc ttc tgc gag ctc aca ggc tac ggt cgc acc gag gtc atg cag aag           192
Gly Phe Cys Glu Leu Thr Gly Tyr Gly Arg Thr Glu Val Met Gln Lys
         50                  55                  60 acc tgc agc tgc cgt ttc ctc tac ggc cca gag acc agt gag cca gcc           240
Thr Cys Ser Cys Arg Phe Leu Tyr Gly Pro Glu Thr Ser Glu Pro Ala
 65                  70                  75 ctg cag cgt ctg cac aaa gcc ctg gag ggc cac cag gag cac cgg gct           288
Leu Gln Arg Leu His Lys Ala Leu Glu Gly His Gln Glu His Arg Ala
                     85                  90                  95 gaa atc tgc ttc tac cgc aag gat ggc tca gcc ttt tgg tgc ctc ctg           336
Glu Ile Cys Phe Tyr Arg Lys Asp Gly Ser Ala Phe Trp Cys Leu Leu
                100                 105                 110 gac atg atg ccc atc aag aat gag atg ggg gag gtc gtg ctg ttc ctc           384
Asp Met Met Pro Ile Lys Asn Glu Met Gly Glu Val Val Leu Phe Leu
            115                 120                 125 ttt tcc ttc aag gat atc act cag agt gga agc cca gga ctt ggc ccc           432
```

```
Phe Ser Phe Lys Asp Ile Thr Gln Ser Gly Ser Pro Gly Leu Gly Pro
            130                 135                 140 caa gga ggc cgc ggg gac agt aat cac gaa aac tcc ctt ggt aga agg       480
Gln Gly Gly Arg Gly Asp Ser Asn His Glu Asn Ser Leu Gly Arg Arg
145                 150                 155 gga gcc acc tgg aaa ttt cgg tct gcc aga aga cgg agc cgt act gtc       528
Gly Ala Thr Trp Lys Phe Arg Ser Ala Arg Arg Arg Ser Arg Thr Val
160                 165                 170                 175 cta cac cga ctg acc ggc cac ttt ggc cgc cgg ggc cag gga ggc atg       576
Leu His Arg Leu Thr Gly His Phe Gly Arg Arg Gly Gln Gly Gly Met
                180                 185                 190 aag gcc aat aat aac gtg ttt gag cca aag cca tca gtg ccc gag tac       624
Lys Ala Asn Asn Asn Val Phe Glu Pro Lys Pro Ser Val Pro Glu Tyr
            195                 200                 205 aag gtg gcc tcc gtg ggg ggg tct cgc tgc ctc ctc ctc cac tac agc       672
Lys Val Ala Ser Val Gly Gly Ser Arg Cys Leu Leu Leu His Tyr Ser
        210                 215                 220 gtc tcc aag gcc atc tgg gac ggc ctt atc ctc ctt gcc acc ttc tac       720
Val Ser Lys Ala Ile Trp Asp Gly Leu Ile Leu Leu Ala Thr Phe Tyr
    225                 230                 235 gtt gcg gtc acc gtc ccc tac aat gtc tgt ttc tcg ggt gac gat gac       768
Val Ala Val Thr Val Pro Tyr Asn Val Cys Phe Ser Gly Asp Asp Asp
240                 245                 250                 255 acc ccc atc act tcg cga cac acc ctt gtc agc gac atc gcc gtg gaa       816
Thr Pro Ile Thr Ser Arg His Thr Leu Val Ser Asp Ile Ala Val Glu
                260                 265                 270 atg ctc ttc atc cta gat atc atc ctg aac ttc cgc acc acc tat gtg       864
Met Leu Phe Ile Leu Asp Ile Ile Leu Asn Phe Arg Thr Thr Tyr Val
            275                 280                 285 tcc cag tcc ggc cag gta atc tct gct cct cgt tcc att ggc ctc cac       912
Ser Gln Ser Gly Gln Val Ile Ser Ala Pro Arg Ser Ile Gly Leu His
        290                 295                 300 tac ctg gcc acc tgg ttc ttc atc gac ctt att gct gct ctg ccc ttt       960
Tyr Leu Ala Thr Trp Phe Phe Ile Asp Leu Ile Ala Ala Leu Pro Phe
    305                 310                 315 gac ctg ctt tac atc ttc aac atc acc gtg acc tcg ctg gtg cac cta      1008
Asp Leu Leu Tyr Ile Phe Asn Ile Thr Val Thr Ser Leu Val His Leu
320                 325                 330                 335 ctg aag aca gtg cgg ctg ttg cgg ctg ctg cgg ctg ctg cag aag ctg      1056
Leu Lys Thr Val Arg Leu Leu Arg Leu Leu Arg Leu Leu Gln Lys Leu
                340                 345                 350 gag cgg tac tct cag tgc agt gct gtg gtg ctc acg ctg ctc atg tcg      1104
Glu Arg Tyr Ser Gln Cys Ser Ala Val Val Leu Thr Leu Leu Met Ser
            355                 360                 365 gtc ttt gcg ctc ctt gcc cac tgg atg gcc tgc atc tgg tat gtc atc      1152
Val Phe Ala Leu Leu Ala His Trp Met Ala Cys Ile Trp Tyr Val Ile
        370                 375                 380 ggg cgc cgg gag atg gag gcc aat gac ccg ctg ctc tgg gac att ggc      1200
Gly Arg Arg Glu Met Glu Ala Asn Asp Pro Leu Leu Trp Asp Ile Gly
    385                 390                 395 tgg ttg cat gag ttg ggc aag cgt ctg gag gtg ccc tat gtc aat ggc      1248
Trp Leu His Glu Leu Gly Lys Arg Leu Glu Val Pro Tyr Val Asn Gly
400                 405                 410                 415 tcg gtg ggc ggc cca tca cgg cgc agc gcc tac atc gcg gca ctg tac      1296
Ser Val Gly Gly Pro Ser Arg Arg Ser Ala Tyr Ile Ala Ala Leu Tyr
                420                 425                 430 ttc act cta agc agc ctc acc agt gtg ggc ttt ggc aac gtg tgt gcc      1344
Phe Thr Leu Ser Ser Leu Thr Ser Val Gly Phe Gly Asn Val Cys Ala
            435                 440                 445
```

```
aac acc gac gcg gag aag atc ttc tcc atc tgc acg atg ctc ata ggc   1392
Asn Thr Asp Ala Glu Lys Ile Phe Ser Ile Cys Thr Met Leu Ile Gly
        450                 455                 460 gcc ctg atg cac gct gtg gtg ttc ggg aac gtg aca gcc atc atc cag   1440
Ala Leu Met His Ala Val Val Phe Gly Asn Val Thr Ala Ile Ile Gln
465                 470                 475 cgc atg tac tcg cgc cgc tcg ctc tac cac agc cgc atg aag gac ctc   1488
Arg Met Tyr Ser Arg Arg Ser Leu Tyr His Ser Arg Met Lys Asp Leu
480                 485                 490                 495 aag gac ttc atc cgt gtg cac cgc ctg ccg cgg ccg ctc aag cag cgc   1536
Lys Asp Phe Ile Arg Val His Arg Leu Pro Arg Pro Leu Lys Gln Arg
                500                 505                 510 atg ctc gaa tac ttc cag acc acg tgg gcc gtc aac agc ggc atc gac   1584
Met Leu Glu Tyr Phe Gln Thr Thr Trp Ala Val Asn Ser Gly Ile Asp
            515                 520                 525 gcc aac gag tta ctg cgt gac ttc cca gac gag ctg aga gct gac att   1632
Ala Asn Glu Leu Leu Arg Asp Phe Pro Asp Glu Leu Arg Ala Asp Ile
        530                 535                 540 gct atg cac ctg aat cgg gag atc ctg cag ctg ccg ttg ttc ggg gca   1680
Ala Met His Leu Asn Arg Glu Ile Leu Gln Leu Pro Leu Phe Gly Ala
545                 550                 555 gcg agc agg ggc tgc ctg cgg gcc cta tcg ctg cac atc aag acc tcg   1728
Ala Ser Arg Gly Cys Leu Arg Ala Leu Ser Leu His Ile Lys Thr Ser
560                 565                 570                 575 ttc tgc gct ccg ggc gag tac ctg ttg cgc cgt ggg gat gcc ctg cag   1776
Phe Cys Ala Pro Gly Glu Tyr Leu Leu Arg Arg Gly Asp Ala Leu Gln
                580                 585                 590 gca cat tac tat gtc tgc tcc ggc tcg ctt gag gtg ctc cga gac aac   1824
Ala His Tyr Tyr Val Cys Ser Gly Ser Leu Glu Val Leu Arg Asp Asn
            595                 600                 605 atg gtg ctg gcc atc ctg ggg aag ggg gac ctg att gga gca gat atc   1872
Met Val Leu Ala Ile Leu Gly Lys Gly Asp Leu Ile Gly Ala Asp Ile
        610                 615                 620 cct gag ccg ggg cag gag cct ggg ttg gga gca gac cca aac ttc gtg   1920
Pro Glu Pro Gly Gln Glu Pro Gly Leu Gly Ala Asp Pro Asn Phe Val
625                 630                 635 cta aag acc agt gct gat gtg aaa gct ctg acc tac tgt ggc ctg cag   1968
Leu Lys Thr Ser Ala Asp Val Lys Ala Leu Thr Tyr Cys Gly Leu Gln
640                 645                 650                 655 cag ctg agc agc cga ggg ctg gct gag gtc ctg agg ctc tat cct gag   2016
Gln Leu Ser Ser Arg Gly Leu Ala Glu Val Leu Arg Leu Tyr Pro Glu
                660                 665                 670 tat ggg gct gcc ttc cgg gct ggc ctg ccc cgg gac ctc acc ttc aac   2064
Tyr Gly Ala Ala Phe Arg Ala Gly Leu Pro Arg Asp Leu Thr Phe Asn
            675                 680                 685 ctg cgc cag ggc tct gac acc agt ggc ctc agc cgc ttt tcc cga tcc   2112
Leu Arg Gln Gly Ser Asp Thr Ser Gly Leu Ser Arg Phe Ser Arg Ser
        690                 695                 700 cct cgc ctc tcc cag ccc cgc tca gaa agc ctc ggc tcc tca gac       2160
Pro Arg Leu Ser Gln Pro Arg Ser Glu Ser Leu Gly Ser Ser Asp
705                 710                 715 aag acg ctg cca tcc atc aca gag gcc gag agt ggc gcg gag cct ggg   2208
Lys Thr Leu Pro Ser Ile Thr Glu Ala Glu Ser Gly Ala Glu Pro Gly
720                 725                 730                 735 ggt ggt ccc agg ccc cga cgg ccc ctc ctg ctc ccc aac ctc agc cca   2256
Gly Gly Pro Arg Pro Arg Arg Pro Leu Leu Leu Pro Asn Leu Ser Pro
                740                 745                 750 gca cgg cct cgg ggc tcc ctg gtc agc ctt ttg ggc gag gag ctg ccc   2304
Ala Arg Pro Arg Gly Ser Leu Val Ser Leu Leu Gly Glu Glu Leu Pro
            755                 760                 765
```

```
cca ttc tca gcc ctt gtc tcc tct cct tcc tta tcc cca tcc ctg tcc    2352
Pro Phe Ser Ala Leu Val Ser Ser Pro Ser Leu Ser Pro Ser Leu Ser
        770                 775                 780 cct gcc ctg gct ggc cag ggc cac agt gcc tcc cct cac ggc ccc ccc    2400
Pro Ala Leu Ala Gly Gln Gly His Ser Ala Ser Pro His Gly Pro Pro
        785                 790                 795 agg tgc tct gct gcc tgg aag ccc cct cag ctt ctc att ccc cca ctg    2448
Arg Cys Ser Ala Ala Trp Lys Pro Pro Gln Leu Leu Ile Pro Pro Leu
800                 805                 810                 815 gga acc ttt gga cct ccg gac ctc agt ccc cgg ata gtg gat ggc att    2496
Gly Thr Phe Gly Pro Pro Asp Leu Ser Pro Arg Ile Val Asp Gly Ile
                820                 825                 830 gag gac tct ggc agc aca gct gag gcc cct tca ttc cga ttc agc agg    2544
Glu Asp Ser Gly Ser Thr Ala Glu Ala Pro Ser Phe Arg Phe Ser Arg
            835                 840                 845 agg cct gaa ctg cca agg ccc cgc tcc cag gcg ccc cct aca ggg acc    2592
Arg Pro Glu Leu Pro Arg Pro Arg Ser Gln Ala Pro Pro Thr Gly Thr
        850                 855                 860 agg ccc agc cca gaa ttg gcc agt gag gct gag gag gtg aag gaa aag    2640
Arg Pro Ser Pro Glu Leu Ala Ser Glu Ala Glu Glu Val Lys Glu Lys
    865                 870                 875 gtt tgc cgg ctg aac cag gag atc tct cgt ctc aat cag gag gtg tct    2688
Val Cys Arg Leu Asn Gln Glu Ile Ser Arg Leu Asn Gln Glu Val Ser
880                 885                 890                 895 cag ctt agc cgg gag ctg cgg cac atc atg ggc ctg ctg cag gcc agg    2736
Gln Leu Ser Arg Glu Leu Arg His Ile Met Gly Leu Leu Gln Ala Arg
                900                 905                 910 ctg ggt ccc cca ggc cac cca gca ggc tcc gct tgg acc cca gac cct    2784
Leu Gly Pro Pro Gly His Pro Ala Gly Ser Ala Trp Thr Pro Asp Pro
            915                 920                 925 cct tgt cca cag ctg agg cca cca tgc ctc tct cct tgt gcg tcc aga    2832
Pro Cys Pro Gln Leu Arg Pro Pro Cys Leu Ser Pro Cys Ala Ser Arg
        930                 935                 940 cca cca ccc agc ctc cag gat act acg ctt gct gaa gtt cac tgc cca    2880
Pro Pro Pro Ser Leu Gln Asp Thr Thr Leu Ala Glu Val His Cys Pro
    945                 950                 955 gcc agt gtg ggg acc atg gag aca ggg act gcg ctc ctg gac ttg aga    2928
Ala Ser Val Gly Thr Met Glu Thr Gly Thr Ala Leu Leu Asp Leu Arg
960                 965                 970                 975 cct tcc ata ttg ccc ccc tac ccc tca gag cct gac cct ctg gga ccc    2976
Pro Ser Ile Leu Pro Pro Tyr Pro Ser Glu Pro Asp Pro Leu Gly Pro
                980                 985                 990 tct cca gtg cca gag gcc tca ccc cca acc cca agc ctc ttg agg cac    3024
Ser Pro Val Pro Glu Ala Ser Pro Pro Thr Pro Ser Leu Leu Arg His
            995                 1000                1005 agt ttc cag tcc agg tca gac aca ttc cac tga ccctggc                3064
Ser Phe Gln Ser Arg Ser Asp Thr Phe His
        1010                1015

<210> SEQ ID NO 6
<211> LENGTH: 1017
<212> TYPE: PRT
<213> ORGANISM: Homo sapiens

<400> SEQUENCE: 6

Met Pro Val Met Lys Gly Leu Leu Ala Pro Gln Asn Thr Phe Leu Asp
 1               5                  10                  15

Thr Ile Ala Thr Arg Phe Asp Gly Thr His Ser Asn Phe Leu Leu Ala
            20                  25                  30
```

-continued

```
Asn Ala Gln Gly Thr Arg Gly Phe Pro Ile Val Tyr Cys Ser Asp Gly
         35                  40                  45

Phe Cys Glu Leu Thr Gly Tyr Gly Arg Thr Glu Val Met Gln Lys Thr
 50                  55                  60

Cys Ser Cys Arg Phe Leu Tyr Gly Pro Glu Thr Ser Glu Pro Ala Leu
 65                  70                  75                  80

Gln Arg Leu His Lys Ala Leu Glu Gly His Gln Glu His Arg Ala Glu
                 85                  90                  95

Ile Cys Phe Tyr Arg Lys Asp Gly Ser Ala Phe Trp Cys Leu Leu Asp
                100                 105                 110

Met Met Pro Ile Lys Asn Glu Met Gly Glu Val Val Leu Phe Leu Phe
             115                 120                 125

Ser Phe Lys Asp Ile Thr Gln Ser Gly Ser Pro Leu Gly Pro Gln
 130                 135                 140

Gly Gly Arg Gly Asp Ser Asn His Glu Asn Ser Leu Gly Arg Arg Gly
145                 150                 155                 160

Ala Thr Trp Lys Phe Arg Ser Ala Arg Arg Ser Arg Thr Val Leu
                 165                 170                 175

His Arg Leu Thr Gly His Phe Gly Arg Arg Gly Gln Gly Gly Met Lys
             180                 185                 190

Ala Asn Asn Asn Val Phe Glu Pro Lys Pro Ser Val Pro Glu Tyr Lys
         195                 200                 205

Val Ala Ser Val Gly Gly Ser Arg Cys Leu Leu His Tyr Ser Val
 210                 215                 220

Ser Lys Ala Ile Trp Asp Gly Leu Ile Leu Ala Thr Phe Tyr Val
225                 230                 235                 240

Ala Val Thr Val Pro Tyr Asn Val Cys Phe Ser Gly Asp Asp Thr
                 245                 250                 255

Pro Ile Thr Ser Arg His Thr Leu Val Ser Asp Ile Ala Val Glu Met
             260                 265                 270

Leu Phe Ile Leu Asp Ile Ile Leu Asn Phe Arg Thr Thr Tyr Val Ser
         275                 280                 285

Gln Ser Gly Gln Val Ile Ser Ala Pro Arg Ser Ile Gly Leu His Tyr
     290                 295                 300

Leu Ala Thr Trp Phe Phe Ile Asp Leu Ile Ala Ala Leu Pro Phe Asp
305                 310                 315                 320

Leu Leu Tyr Ile Phe Asn Ile Thr Val Thr Ser Leu Val His Leu Leu
                 325                 330                 335

Lys Thr Val Arg Leu Leu Arg Leu Leu Arg Leu Leu Gln Lys Leu Glu
             340                 345                 350

Arg Tyr Ser Gln Cys Ser Ala Val Leu Thr Leu Met Ser Val
         355                 360                 365

Phe Ala Leu Leu Ala His Trp Met Ala Cys Ile Trp Tyr Val Ile Gly
 370                 375                 380

Arg Arg Glu Met Glu Ala Asn Asp Pro Leu Leu Trp Asp Ile Gly Trp
385                 390                 395                 400

Leu His Glu Leu Gly Lys Arg Leu Glu Val Pro Tyr Val Asn Gly Ser
                 405                 410                 415

Val Gly Gly Pro Ser Arg Arg Ser Ala Tyr Ile Ala Ala Leu Tyr Phe
             420                 425                 430

Thr Leu Ser Ser Leu Thr Ser Val Gly Phe Gly Asn Val Cys Ala Asn
         435                 440                 445

Thr Asp Ala Glu Lys Ile Phe Ser Ile Cys Thr Met Leu Ile Gly Ala
```

-continued

```
            450                 455                 460
Leu Met His Ala Val Val Phe Gly Asn Val Thr Ala Ile Ile Gln Arg
465                 470                 475                 480
Met Tyr Ser Arg Arg Ser Leu Tyr His Ser Arg Met Lys Asp Leu Lys
                485                 490                 495
Asp Phe Ile Arg Val His Arg Leu Pro Arg Pro Leu Lys Gln Arg Met
                500                 505                 510
Leu Glu Tyr Phe Gln Thr Thr Trp Ala Val Asn Ser Gly Ile Asp Ala
                515                 520                 525
Asn Glu Leu Leu Arg Asp Phe Pro Asp Glu Leu Arg Ala Asp Ile Ala
        530                 535                 540
Met His Leu Asn Arg Glu Ile Leu Gln Leu Pro Leu Phe Gly Ala Ala
545                 550                 555                 560
Ser Arg Gly Cys Leu Arg Ala Leu Ser Leu His Ile Lys Thr Ser Phe
                565                 570                 575
Cys Ala Pro Gly Glu Tyr Leu Leu Arg Arg Gly Asp Ala Leu Gln Ala
                580                 585                 590
His Tyr Tyr Val Cys Ser Gly Ser Leu Glu Val Leu Arg Asp Asn Met
            595                 600                 605
Val Leu Ala Ile Leu Gly Lys Gly Asp Leu Ile Gly Ala Asp Ile Pro
    610                 615                 620
Glu Pro Gly Gln Glu Pro Gly Leu Gly Ala Asp Pro Asn Phe Val Leu
625                 630                 635                 640
Lys Thr Ser Ala Asp Val Lys Ala Leu Thr Tyr Cys Gly Leu Gln Gln
                645                 650                 655
Leu Ser Ser Arg Gly Leu Ala Glu Val Leu Arg Leu Tyr Pro Glu Tyr
                660                 665                 670
Gly Ala Ala Phe Arg Ala Gly Leu Pro Arg Asp Leu Thr Phe Asn Leu
            675                 680                 685
Arg Gln Gly Ser Asp Thr Ser Gly Leu Ser Arg Phe Ser Arg Ser Pro
    690                 695                 700
Arg Leu Ser Gln Pro Arg Ser Glu Ser Leu Gly Ser Ser Ser Asp Lys
705                 710                 715                 720
Thr Leu Pro Ser Ile Thr Glu Ala Glu Ser Gly Ala Glu Pro Gly Gly
                725                 730                 735
Gly Pro Arg Pro Arg Pro Leu Leu Leu Pro Asn Leu Ser Pro Ala
            740                 745                 750
Arg Pro Arg Gly Ser Leu Val Ser Leu Leu Gly Glu Leu Pro Pro
    755                 760                 765
Phe Ser Ala Leu Val Ser Pro Ser Leu Ser Pro Ser Leu Ser Pro
    770                 775                 780
Ala Leu Ala Gly Gln Gly His Ser Ala Ser Pro His Gly Pro Pro Arg
785                 790                 795                 800
Cys Ser Ala Ala Trp Lys Pro Pro Gln Leu Leu Ile Pro Pro Leu Gly
                805                 810                 815
Thr Phe Gly Pro Pro Asp Leu Ser Pro Arg Ile Val Asp Gly Ile Glu
                820                 825                 830
Asp Ser Gly Ser Thr Ala Glu Ala Pro Ser Phe Arg Phe Ser Arg Arg
            835                 840                 845
Pro Glu Leu Pro Arg Pro Arg Ser Gln Ala Pro Pro Thr Gly Thr Arg
    850                 855                 860
Pro Ser Pro Glu Leu Ala Ser Glu Ala Glu Val Lys Glu Lys Val
865                 870                 875                 880
```

-continued

```
Cys Arg Leu Asn Gln Glu Ile Ser Arg Leu Asn Gln Glu Val Ser Gln
                885                 890                 895

Leu Ser Arg Glu Leu Arg His Ile Met Gly Leu Leu Gln Ala Arg Leu
            900                 905                 910

Gly Pro Pro Gly His Pro Ala Gly Ser Ala Trp Thr Pro Asp Pro Pro
            915                 920                 925

Cys Pro Gln Leu Arg Pro Pro Cys Leu Ser Pro Cys Ala Ser Arg Pro
            930                 935                 940

Pro Pro Ser Leu Gln Asp Thr Thr Leu Ala Glu Val His Cys Pro Ala
945                 950                 955                 960

Ser Val Gly Thr Met Glu Thr Gly Thr Ala Leu Leu Asp Leu Arg Pro
                965                 970                 975

Ser Ile Leu Pro Pro Tyr Pro Ser Glu Pro Asp Pro Leu Gly Pro Ser
            980                 985                 990

Pro Val Pro Glu Ala Ser Pro Pro Thr Pro Ser Leu Leu Arg His Ser
            995                 1000                1005

Phe Gln Ser Arg Ser Asp Thr Phe His
    1010                1015
```

```
<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence:Primer

<400> SEQUENCE: 7
gccatgccgg tcatgaagg                                                        19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 8
gccagggtca gtggaatgtg                                                       20

<210> SEQ ID NO 9
<211> LENGTH: 3715
<212> TYPE: DNA
<213> ORGANISM: Rattus sp.

<400> SEQUENCE: 9
ctgctggggc ctacgaacct gggccgggca tagcccccccg acggctactc tagggggcgc          60
ggggcccggc gggggggcggc cgagccaggc gccctccccc ggcgctgagt ccccgcgccc         120
cggagggatg gggcgggcgg tccccgccgc ctaagatgcc ggccatgcgg gggctccttg         180
cgccgcagaa caccttcctg acaccatcg ccacccgctt cgacgggacg cacagtaact          240
tcgtcctggg caacgcccag gtggcaggc tcttccctgt ggtctactgc tccgatggct          300
tctgtgacct cacgggtttc tccagagctg aggtcatgca gcgaggctgt gcctgctcct          360
tcctctatgg gccagacacc agtgagttgg tccgccaaca gatccgaaaa gccctggatg         420
agcacaaaga attcaaggct gaactgatcc tgtaccggaa gagcgggctt ccattctggt         480
gtctcctgga tgtgatacct ataaaaaacg agaaggggga ggtggccctc ttcctggtct         540
ctcacaagga catcagtgag accaagaacc gaggaggccc tgacaactgg aaggagagag         600
```

-continued

| | |
|---|---|
| gtggtggccg acgcagatat ggtcgggcag gatccaaagg ctttaatgcc aatcggaggc | 660 |
| gcagccgggc ggttctctac cacctctctg gtcacctgca gaaacaaccc aagggcaagc | 720 |
| acaaactcaa taagggtgtg tttggagaga agccaaattt gcccgaatat aaagtcgctg | 780 |
| ctatccggaa gtcacccttt atcctgctgc actgtgggc tctgagagcc acctgggatg | 840 |
| gcttcatcct gctcgccacg ctctacgtgg ctgtcactgt gccatacagc gtgtgtgtga | 900 |
| gcacagcacg ggagcccagt gctgcccgtg gcccacctag tgtctgtgac ctggccgtgg | 960 |
| aagtcctctt catcttagat attgtgctga attttcgtac tacatttgtg tccaagtcag | 1020 |
| gccaggtggt attcgcccca aagtccattt gcctccacta cgtcaccacc tggttcctgc | 1080 |
| tggatgtcat agcagcactg ccctttgacc tactacatgc cttcaaggtc aatgtgtacg | 1140 |
| ttggggctca cctactgaag accgtgcggc tgcttcggct gctgcgccta ctaccaagac | 1200 |
| tggaccggta ctctcagtat agcgctgttg tgctcacctt gctcatggct gtgtttgccc | 1260 |
| tgctcgccca ctgggtggcc tgcgtttggt tctacatcgg ccagcaagag attgagaaca | 1320 |
| gcgagtcaga gctgcctgag atcggctggc tgcaggagtc ggcacgcagg ctggagacgc | 1380 |
| cctattacct ggtgagccgg agtccagatg gagggaacag ctctggccag agtgaaaact | 1440 |
| gcagtagcag tggcggcggc agcgaagcca acgggactgg gctggagctg ctgggtggcc | 1500 |
| catccctacg cagcgcctac atcacctcct tgtacttcgc gctcagcagt ctcaccagtg | 1560 |
| tgggcttcgg caatgtgtcc gctaacacag acactgagaa gatttttctcc atctgccacca | 1620 |
| tgcttattgg agctctgatg catgcagtgg tgtttgggaa tgtgacagcc atcatccagc | 1680 |
| gcatgtacgc tcgccgcttt ctgtaccaca gccgcacccg tgacctgcga gactacattc | 1740 |
| gcatccaccg catccccaag cccctcaagc agcgcatgct cgagtacttc caagccacct | 1800 |
| gggccgtgaa caacggcatc gataccactg agctgctgca gagccttccg gatgagcttc | 1860 |
| gagcagacat cgccatgcac ctgcacaagg aggtcctgca gctgccattg ttcgaggcag | 1920 |
| cgagccgtgg ctgcctgcgg gcactgtctc tggccctgag gccgccttc tgcacgccgg | 1980 |
| gcgagtacct cattcaccaa ggcgatgctc tccaggctct ctactttgtg tgctcaggtt | 2040 |
| ccatggaggt cctcaaaggt ggcaccgtcc tcgccattct agggaagggt gacctgatcg | 2100 |
| gctgtgagct gccccagcga gagcaagtag tgaaggccaa tgccgacgta aagggctga | 2160 |
| catactgcgt cctacagtgc ctgcagctgg ctgggctgca cgagagcctc gcactgtacc | 2220 |
| ctgagtttgc cccacgcttt agccgtggcc tccagggga gctcagctac aacctgggag | 2280 |
| ctggaggagt gtctgcagag gtggatacca gctcactgag tggtgacaac accctcatgt | 2340 |
| ccacactgga ggagaaggag acagatgggg agcaaggaca cacgatctca ccagcccag | 2400 |
| cagatgagcc ctccagcccc ctgctgtcac ctggctgtac ctcctcctcc tcagcggcca | 2460 |
| aactactctc cccacgtcga actgcacccc ggccgaggct gggtggcaga gggcggccaa | 2520 |
| gtagggcagg ggttttgaag cctgaggctg gtccttctgc tcatccacgg acacttgatg | 2580 |
| ggttgcagct gccccccatg ccatggaatg tacctccaga cctgagcccc aggtcgtag | 2640 |
| atggcattga ggatggctgc ggctctgacc agcacaagtt ctctttccgg gtgggtcagt | 2700 |
| ctggcccaga atgtagcagc agcccctccc caggaacaga gagtggcctg ctcactgtcc | 2760 |
| ccttggtgcc cagtgaggca agaaacacag acacactgga caagctacgg caggcggtga | 2820 |
| cggagctgtc tgaacaggtg ctgcagatgc gagagggact gcagtcactt cgccaggctg | 2880 |
| tgcagctcat cctggtgccc caaggggaag gccagtgtcc ccgggtatca ggagagggc | 2940 |

```
catgcccagc cactgcctct gggctcctac aacccctgcg tgtggacact ggggcatcat    3000
cctactgcct gcagccccca gcaggttcag tcttgagtgg gacctggcct caccccgtc     3060 cagggcatcc ccctcccctc atggcaccct ggccctgggg cccccagca tctcagagct     3120 ccccctggcc tcgagccaca gctttatgga cctccacctc agactcagag ccccctggct    3180
ctggagacct ctgctctgag cccagcaccc cagcctcacc cctcctcct gaggaaggag     3240 ctaggactgg gactcctgca cctgtgagcc aggctgaggc taccagtact ggagagcccc    3300
ctccggggtc agggggccga gccttgccct gggatcccca cagcctagag atggtgctca    3360
tcggctgcca tggccctggc tcggtccagt ggacccagga ggagggcaca ggagtctgac    3420
cacaggcagg gagagggtt ctgcaaacac ccgccacctg ctgaccgccc agcctcacag     3480
ggctgccctc tggctcaggg cagggaacct aaggaaggag gagggtgagc tggagcctca    3540
ggccccaggc cagggatcca cggttctgc tccactgacc tgacccaatg ggggcagagg     3600
cctgaggacg aggagggtt ctgccattcc ttgcatgtgc ccatctccac tgtcctctgt     3660
cctcatgttt tttatattaa aaacataaa aaaaaccaa taaagaaact acttt          3715
```

<210> SEQ ID NO 10
<211> LENGTH: 3736
<212> TYPE: DNA
<213> ORGANISM: Rattus sp.

<400> SEQUENCE: 10

```
caggcagcgg cggcgagagg aggggaggag gcaggccggc gcatggggcg ccccggcccc      60
gccggtagcg cgccccctcc ggccaggccg cgctgaacgc agcccgcgca acgcctcgaa     120
ttcgtacccg gggccatgcc ggtcatgaag gggttgctgg ccccgcaaaa caccttttctg    180 gacaccatcg ccactcgctt tgacggcacg cacagcaact ttcttctggc caatgcccag    240
ggcccacggg gttttcccat cgtctactgc tctgacggct ctgtgagct cacaggctac     300 ggccgcaccg aggtcatgca gaaaacctgt agctgccggt tcctctatgg cccagagacc    360
agtgagccgc ccttgcaacg gttacaaaaa gccctgagg gccaccaaga acacagagct    420
gaaatctgct tttaccgaaa ggatggctcg gcctttggt gtcttctgga catgatgccc     480
atcaaaaatg agctggggga ggtggtgctt ttcctatttt cctttaagga catctctcag    540
agtggaggcc caggacttgg ctcaccaggg atccatgggg acaataataa tcatgaaaac   600
tcccttggga ggagaggagc tagctcaaga cttaggtcca cgaggaggca gaaccggaca     660
gttctacacc ggttgactgg ccactttggt cgccgggacc agggaagcgt gaaagccaat    720
agtaacgtgt ttgagccaaa gccatcagtg cctgagtaca aagtggcctc cgtgggggc     780 tcccgctgcc tgctcctcca ctacagcatc cccaaggctg tctgggacgg tctcatcctt     840
ctcgctacgt tctacgtcgc ggtcaccgtc ccttacaacg tctgcttcgc tggtgatgac    900 gacacccca tcacgtcccg acacacccctt gtcagtgaca tcgctgtgga gatgctcttc    960
atcctggaca tcatcttgaa cttccgcacc acctacgtgt cccagtcggg ccaggtggtt   1020
tctgctcctc ggtccattgg cctccactac ctggccacct ggttcttcgt ggacctcatt   1080
gctgctttgc cctttgacct gctgtatgtc ttcaacatca ctgtgacctc gctggtacat    1140
ctgctgaaaa ccgtgcggct cctgcggttg ctgaggctgc tgcagaagct agagcggtac   1200
tctcagtgca gcgcggtggt gctcacgctg ctcatgtccg tctttgcact ccttgcccac   1260
tggatggcct gcgtctggta tgtcatcggg cgccgggaga tggaggccaa tgaccgctg     1320 ctctgggaca ttggttggtt gcatgagctg ggtaagcggc tggaggagcc ttatgtcaat   1380
```

```
ggctcggccg gtggaccatc tcggcgcagt gcctacatcg ccgcgctgta cttcacgctg   1440
agcagcctca ccagtgtagg cttcggcaac gtttgtgcca acactgacgc tgagaagatc   1500
ttctccatct gcacgatgct cataggcgcg ctgatgcacg cggtggtgtt tgggaatgtc   1560
acagccatca tccagcgcat gtactcccga cgctcgctct accacagccg catgaaggat   1620
ctcaaggact tcatccgagt gcatcgtctg ccccgcccac tcaagcagcg catgctcgag   1680
tacttccaga ctacatgggc cgtcaacagc ggcatcgatg ccaacgagtt actgcgtgac   1740
ttcccggatg agctgcgagc tgacatcgcc atgcacctga tcgggagat cctgcagctg   1800 cctttgtttg gagcagcaag caggggctgc cttcgtgccc tctccctgca catcaagacc   1860
tcattttgtg ctcctgggga gttcctgcta cgccgtgggg atgccctgca ggcacactac   1920
tatgtctgct ctggctctct tgaggtgctc cgagacaaca cggtgctggc catccttgga   1980
aagggggact tgattgggc agacatccct gagttgggc aggagcctgg ggcaggggca   2040
ggctgcgtgc tgaagaccag cgctgatgtg aaagcactga cttactgcgg cctgcagcag   2100
ctgagcagcc gagggctggc cgaggtcctt cggttgtatc cggaatatgt ggctgccttc   2160
agggctggcc taccccggga cctaaccttc aacctgcgcc aaggctctga aaacaatggc   2220
ctcggccgct tctcacgttc tcctcgactc tcccaggcac gctccgacac tcttggttcc   2280
tcctcagaca agactctgcc atccatcaca gaaaccgagg gtggcatgga gcctggggct   2340
ggttccaagc ccgtcggcc cctcctgctg cccaacctca gtccagcacg acctcggggg   2400
tccctggtca gccttttggg cgaagagctg cccccattct cagcccttgt ctcctctcct   2460
tccctgtccc caactccttc ccctgccctg gctggccggg gttcaagtcc ctccctgcac   2520 gggccccca ggggctctgc tgcctggaag cccccccagc tcctcacccc ccactgggga   2580
acatttggac ctccggacct cagtcccggg atcgtggatg gcattgagga ctccagtaac   2640
acagctgagg ctcctacatt ccggttcagc aagaggccgg agcccaccag aacccgttca   2700
caggctcccc tttcaggccc taggctcagc cgggaactgg ccacagaggc agcagaggag   2760
gtgaaggaaa aggtctgcag gctgaaccaa gagatttcca gactcaacca ggaagtgtct   2820
cagctgagcc gggagcttcg ccaagtgatg ggcctcttac aggccaggct gggtccccca   2880
agtcacccac ctgactccac ttggctccca gaccttcctt gtccccatca gagaccgcca   2940
tgcatctctc ctcatatgtc tggacctcca cctggtctcc agaatactac acttgctgta   3000
gtccactgtc cagccagtgt tgggacagtg gagatagggg ccaccccctc agagctgagg   3060
tcttccatgg tgccaccctt tccctcagaa cctgatcctc ttggaccctc tccagtgcca   3120
gaggcttctc ctctgacccc aagcctcctg aagcacagct ccagtctgg gtcagacaca   3180 ttccactgac cctggccttg ggccaggcc tgtctggggt gggcttaatt acctgccatc   3240
cagggaggag ctgggctcct tggcctcttg ccttggggtc agcagctgcc agctggtctg   3300
gttggctctg gattctctgg actttttaac aatgagtggc cacatctaac cccgttccat   3360
tttctaaacc atccccccca cccgtcctac tcttgtggga gggagtcac ctgaagccgt   3420 ggaatccagc aggcatgaaa tggaccatgg tgccctgttg ggctacgcag aggagatgtc   3480
ttactttctc cccacgactt ggaggctgtc atgcaaggtg gtcccttctg ctgccagcag   3540
ctcaaagcat tctagcttta cccttctgca gttcccacct ccaaacatca gtcatatctg   3600 ccccccctccc tccaacatg gtctcgacct caatgaggat ctgggcaact cacaaaccct   3660
ctctggtttc cagctcccct ttctcactaa acaccccagg ctcacttttg gatagaaaat   3720
```

```
aaatccatat attttt                                              3736

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:probe

<400> SEQUENCE: 11
accttcctgg acaccatcgc                                            20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:probe

<400> SEQUENCE: 12
ccaaacacca ccgcgtgcat                                            20
```